US008329468B2

(12) United States Patent
Takebe

(10) Patent No.: US 8,329,468 B2
(45) Date of Patent: Dec. 11, 2012

(54) METHODS FOR COLLECTING AND USING PLACENTA CORD BLOOD STEM CELL

(75) Inventor: Naoko Takebe, Elkridge, MD (US)

(73) Assignee: Cord Blood Science Inc., Elkridge, MD (US)

( * ) Notice: Subject to any disclaimer, the term of this patent is extended or adjusted under 35 U.S.C. 154(b) by 976 days.

(21) Appl. No.: 12/268,319

(22) Filed: Nov. 10, 2008

(65) Prior Publication Data

US 2009/0123437 A1 May 14, 2009

Related U.S. Application Data

(63) Continuation of application No. PCT/US2007/011359, filed on May 11, 2007.

(60) Provisional application No. 60/799,734, filed on May 11, 2006.

(51) Int. Cl.
*C12N 5/00* (2006.01)
*C12N 5/02* (2006.01)
*A01N 63/00* (2006.01)

(52) U.S. Cl. .............. 435/379; 435/378; 424/93.7
(58) Field of Classification Search ............... 435/379, 435/378; 424/93.7
See application file for complete search history.

(56) References Cited

U.S. PATENT DOCUMENTS

| 7,045,148 B2 | 5/2006 | Hariri |
| 7,060,494 B2 | 6/2006 | Bhat |
| 7,255,879 B2 | 8/2007 | Hariri |
| 7,311,904 B2 | 12/2007 | Hariri |
| 8,057,788 B2 * | 11/2011 | Hariri .................. 424/93.1 |
| 2002/0123141 A1 | 9/2002 | Hariri |
| 2003/0032179 A1 | 2/2003 | Hariri |
| 2003/0180269 A1 | 9/2003 | Hariri |
| 2004/0219136 A1 | 11/2004 | Hariri |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0272148 A1 | 12/2005 | Hariri |
| 2006/0153816 A1 | 7/2006 | Brown et al. |
| 2006/0153818 A1 | 7/2006 | Dhanaraj et al. |
| 2006/0154367 A1 | 7/2006 | Kihm et al. |
| 2006/0182724 A1 | 8/2006 | Riordan |
| 2007/0190649 A1 | 8/2007 | Gage |
| 2008/0131410 A1 | 6/2008 | Hariri |

FOREIGN PATENT DOCUMENTS

| CN | 15448029 | 5/2003 |
| WO | 02/064755 A2 | 8/2002 |
| WO | 03/068937 A2 | 8/2003 |
| WO | 2007/047468 A2 | 4/2007 |
| WO | 2007/078183 A2 | 7/2007 |

OTHER PUBLICATIONS

Almeida-Porada, G., et al. Formation of human hepatocytes by human hematopoietic stem cells in sheep. Blood Jul. 2004, 104, pp. 2582-2590, Washington, DC.

Azizi, S.A, et al., Engraftment and migration of human bone marrow stromal cells implanted in the brains of albin rats-similarities to astrocyte grafts, Proc Natl Acad (1998), pp. 3908-3913.
Barker, J.N., et al., (2002). Searching for unrelated donor hematopoietic stem cells: availability and speed of umbilical cord blood versus bone marrow, Biol Blood Marrow Tr, 8(5:257-260, abstract only.
Belvedere O., et al., Increased Blood Volume and CD34+CD38⁻ Progenitor Cell Receovery using a Novel Umbilical Cord Blood Collection System, Stem Cell 2000; 18 pp. 245-251.
Bertolini, F. et al., Comparative study of different procedures for the collection and banking of umbilical cord blood., J Hematother Feb. 1995;4(1) pp.1-2, p. 245-251.
Bhattacharya, S. et al., Direct identification and enrichment of retinal stem cells/progenitors by hoechst dye efflux assay, Invest Ophthalmol Vis Sci vol. 44 Jun. (2003), pp. 2764-2773.
Bicknese, A.R. et al., Human umbilical cord blood cells can be induced to express markers for neurons and glia. Cell Transplant 11, (2002) 261-264.
Brazelton, T.R., et al., From marrow to brain: expression of neuronal phenotypes in adult mice. Science 290, (2000) 1775-1779.
Cai, J., et al., Membrane poperties of rat embryonic multipotent neural stem cells. International Society for Neurochemistry, J Neurochem 2004, 88, pp. 212-226.
Cai, J., et al., In search of "stemness".International Society for Exp Hematology, Elsevier Inc. 32, pp. 585-598, 2004.
Cai, J., et al., Properties of a fetal multipotent neural stem cell (NEP cell). Dev Biol 251, 221-240. (2002).
Camargo, F.D., et al.,Hematopoietic cells are the major source of hepatocyte fusion partners. J Clin Invest 113, 1266-1270 (2004).
Chen, N. et al., Human Umbilical Cord Blood Progenitors: The Potential of These Hematopoietic Cells to Become Neural. Stem cells (Dayton, Ohio), (2005), vol. 23, pp. 1560-1570.
Cogle, C.R. et al., Bone marrow transdifferentiation in brain after transplantation: a retrospective study. Lancet 363, 1432-1437 (2004).
Corti, S. et al., Transplanted ALDHhiSSClo neural stem cells generate motor neurons and delay disease progression of nmd mice, an animal model of SMARD1. Hum Mol Genet 15 2006, pp. 167-187.
Donaldson, C., et al., Impact of obstetric factors on cord blood donation for transplantation. British journal of haematology 106, 128-132, (1999), abstract only.
Eglitis, M.A., et al., Hematopoietic cells differentiate into both microglia in the brains of adult mice. Proc Natl Acad Sci U S A 94, 4080-4085, (1997).
Escolar, M., MD, et al., Tranplantation of umbiiical-cord blood in babies with infantile Krabbe's disease. N Engl J Med 352, 2069-2081, (2005).
Ferrari, G. et al., Muscle regeneration by bone marrow-derived myogenic progenitors. Science 279, 1528-1530, (1998).

(Continued)

*Primary Examiner* — Marcia S Noble
(74) *Attorney, Agent, or Firm* — Kramer & Amado, P.C.

(57) ABSTRACT

An innovative method of collecting cord blood stem cells from an isolated mammalian non-exsanguinated or partially exsanguinated placenta by placental perfusion is described and also an easy method for safe long duration cold storage of the placenta. Placental perfusion can include perfusing the isolated placenta with a pulsatile flow of perfusion solution, for example, using a pulsatile or peristaltic pump or device. The stem cells can then be isolated from the perfusate. Significantly increased amounts of CD133+ stem cells can be collected from the perfusate. The perfusion solution can include an anticoagulant. The isolated mammalian placenta need not be treated with an anticoagulant prior to perfusing. The isolated placenta can be free from an anticoagulant prior to perfusing.

27 Claims, 13 Drawing Sheets

OTHER PUBLICATIONS

Forraz, N. et al. Characterization of a lineage-negative stem-progenitor cell population optimized for ex vivo expansion and enriched for LTC-IC. Stem cells 22, 100-108, 2004

Gage, F. et al., A comparison study of the Belzer machine preservation solution with and without penioillin. Transplant Proc 29, 3643, (1997).

Gekas, C., et al., The placenta is a niche for hematopoietic stem cells. Dev Cell 8, 365-375, (2005).

Gluckman, E. et al., Outcome of cord-bood transplantation from related and unrelated donors, Eurocord Transplant Grp &the Europ Blood & Marrow Transplantation Grp. 337.6, 1997. pp.373-381.

Goodwin HS. et al., Multilineage differentiation activity by cells isolated from umbilical cord blood: . . . Biol Blood Marrow Transplant 7, 581-588 (2001).

Harris, D.T. et al., Collection, separation and cryopreservaton of umbilical cord blood for use in transplantation. Bone marrow transplantation 13, 135-143, (1994).

Hruban, R.H. et al., Fluorescence in situ hybridization for the Y-chromosome can be used to detect cells of recipient origin in allografted . . . Am J pathol 142, 975-980.

Jaatinen, T., et al., Global Gene Expression Profile of Human Cord Blood-Derived CD133+ Cells. Stem Cells 24, 631-641, (2006).

Kim, M. et al., The multidrug resistance transporter ABCG2 (breast cancer resistance protein 1) effluxes Hoechst 33342 and is overexpressed . . . Clin Cancer Res 8, 22-28, 2000.

Korbling, M. et al., Hepatocytes and epithelial cells of donor origin in recipients of peripheral-blood stem cells. N Engl J Med 346, 738-746, (2002).

Kuci, S. et al., Identification of a novel class of human adherent CD34-stem cells that give rise to SCID-repopulating cells. Blood 101, 869-876, (2003).

Kucia, M., et al., Morphological and molecular characterization of novel population of CXCR4(+) SSEA-4(+) Oct-4(+) very small embryonic-like cells . . . Leukemia 2007 297-303.

Kurtzberge, J. et al., Placenta blood as a source of hematopoietic stem cells for transplantation into unrelated recipients. N Engl J Med 335, 157-166, (1996).

Lagassi, E., et al., Purified hematopoietic stem cells can differentiate into hepatocytes in vivo. Nat Med 6, 1229-1234, 2000.

Lasky LC., et al., In utero or ex utero cord blood collection: which is better? Transfusion 42, 1261-1267, 2002.

Laughlin, M.J. et al., Outcomes after tranplantation of cord blood or bone marrow from unrelated donors in adults with leukemia. N Engl J Med 351, 2265-2275, 2004.

Leeser, D.B., et al., Pulsatile pump perfusion of pancreata before human islet cell isolation. Transplant Proc 36, 1050-1051, 2004.

McGuckin, C.P., et al., Umbilical cord blood stem cells can expand hematoptietic and neuroglial progenitors in vitro. Exp Cell Res 295, 350-359, 2004.

McGukin, C.P., et al., Production of stem cells with embryonic characteristics from human umbilical cord blood. Cell Prolif 38, 245-255, 2005.

Mezey, E. et al., Turning blood into brain: cells bearing neuronal antigens generated in vivo from bone marrow. Science 290, 1779-1782. 2000.

Migishima, F. et al., Full reconstitution of hematopoietic system by murine umbilical cord blood. Transplantation 75, 1820-1826 2003.

Müller, P. MD, et al., Cardiomyocytes of noncardiac origin in myocardial biopsies of human transplanted hearts. Circulation 106, 31-35, 2002.

Okamoto, R., et al., Damaged epithelia regenerated by bone marrow-derived cells in the human gastrointestinal tract. Nat Med 8, 1011-1017, 2002.

Ottersbach, K. et al., The murine placenta contains hematopoietic stem cells within the vascular labyrinth region. Dev Cell 8, 377-387, 2005.

Parmar, K. et al., Sca+CD34—murine side population cells are highly enriched for primitive stem cells. Exp Hematol 31, 244-250, 2003.

Parolini, L. et al., Concise Review: Isolation & Characterization of Cells from Human Term Placenta: Outcome of the First International . . . Stem Cells 26, 300-311, 2008.

Petersen, B.E., et al., Bone marrow as a potential source of hepatic oval cells. Science 284, 1168-1170, 1999.

Quaini, F. et al., Chimerism of the transplated heart. N Engl J Med 346, 5-15, 2002.

Rubinstein, P. MD, et al., Outcomes among 562 recipients of placental-blood transplants from unrelated donors. N Engl J Med 339, 1565-1577, 1998.

Rubinstein, P., et al., Stored placental blood for unrelated bone marrow reconstitution. Blood 81, 1679-1690, 1993.

Sanchez-Ramos, et al., Adult bone marrow stromal cells differentiate into neural cells in vitro. Exp Neurol 164, 247-256, 2000.

Sanchez-Ramos, J.R., et al., Neural cells derived from adult bone marrow and umbilical cord blood. J Neurosci Res 69, 880-893, 2002.

Sanchez-Ramos, J.R, Expression of neural markers in human umbilical cord blood. Exp Neurol 171, 109-115, 2001.

Scharenberg, C.W., et al., The ABCG2 transporter is an efficient Hoechst 33342 efflux pump and is preferentially expressed by immature . . . Blood 99, 507-512, 2002.

Shlebak, AA et al., The impact of antenatal and perinatal variables on cord blood haemopoietic stem/progenitor cell yield available . . . Br J Haematol 103, 1167-1171, 1998.

Storms, R. et al., Isolation of primitive human hematopoietic progenitors on the basis of aldehyde dehydrogenase activity, Proc Natl Acad Sci U S A 96, 9118-9123, 1999.

Takebe, N., et al., Methotrexate selection of long-term culture initiating cells following transduction of CD34(+) cells with a . . . Cancer Gene Ther 9, 308-320.ne., 2001.

Takebe, N., et al., Generation of dual resistance to 4-hydroperoxycyclophosphmide and methotrexate by retroviral transfer of the human aldehyde . . . Mol Ther 3, 88-96, 2001.

Theise, N.D., et al., Liver from bone marrow in humans. Hepatology 32, 11-16, 2000.

Turner, CW., et al., A modified harvest technique for cord blood hematopoietic stem cells. Bone marrow transplantation 10, 89-91, 1992.

Wagner, J.E., et al., Transplantation of unrelated donor umbilical cord blood in 102 patients with malignant and diseases: influence . . . Blood 100, 1611-1618 2002.

Wagner, JE., et al., Umbilical cord and placental blood hematopoietic stem cells: collection, cryopreservation, and storage. J Hematother 1, 167-173. 1992.

Wagner, JE., et al., Successful transplantation of HLA-matched and HLA-mismatched umbilical cord blood from unrelatd donors: analysis of engraftment. Blood 88, 795-802, 1996.

Wang, X., et al., Albumin-expressing hepatocyte-like cells develop in the livers of immune-deficient mice that received transplantsof highly . . . Blood 101, 4201-4208, 2003a.

Wang, X., et al., Cell fusion is the principal source of bone-marrow-derived hepatocytes. Nature 422, 897-901, 2003b.

Zhou, S., et al., The ABC Transporter Bcrp 1/ABCG2 is expressed in a wide variety of stem cells and is a molecular determinant of the . . . Nat Med 7, 1028-1034, 2001.

Zigava , T., et al., Human umbilical cord blood cells express neural antigens after transplantation into the deveioping rat brain. Cell Transplant 11, 265-274, 2002.

Fortunel, N.O., et al., Comment"'Stemness': Transcriptioal Profiling of Embryonic and Adult Stem Cells" and "A Stem Cell Molecular Signature". Science 302, Oct. 2003.

George, T.J., et al., "Factors associated with parameters of engraftment potential of umbilical cord blood", Transplanataion and Cellular Engineering, vol. 46, Oct. 2006, abstract only.

Bornstein et al, "A Modified Cord Blood Collection Method Achieves Sufficient Cell Levels for Transplantation in Most Adult Patients", Stem Cells, vol. 23, No. 3. Mar. 2005, pp. 324-334.

Conneally et al., "Expansion In Vitro of Transplantable Human Cord Blood Stem Cells Demonstrated Using A Quantitative Assay of Their Lympho-Myeloid Repopulating Activity in Nonobese Diabetic-Scid/Scid Mice", Proceedings of the National Academy of Sciences of the United States of America, vol. 94, No. 18, 1997, pp. 9836-9841.

Davis et al, "Maximal Cord Blood Recovery and CD34+ Progenitor Cell Collection Using Machine Pulsatile Perfusion of Placentas", Blood, American Society of Hematology, US, vol. 108, No. 11, Part 1, Nov. 2006, p. 1041A.

Takebe et al., "Preliminary Findings on the Use of Pulsatile Machine Reperfusion of a Placenta to Improve the Cord Blood Collection Yield Including Primitive Hematopoietic Stem Cell Fractions", Transfusion, vol. 49, No. 9, Sep. 2009, p. 1911-1916.

Bessems et al., Improved Rat Liver Preservation by Hypthermic Continuous Machine Perfusion Using Poysol, a New, Enriched Preservation Solution, Liver Transplantation, vol. 11, No. 5 May 2005; pp. 539-546.

* cited by examiner

METHODS FOR COLLECTING AND USING PLACENTA CORD BLOOD STEM CELL

This application claims the benefit of PCT Application No. PCT/US2007/011359 filed May 11, 2007 and U.S. Provisional Application No. 60/799,734 filed May 11, 2006. The aforementioned applications are incorporated herein by reference in its entirety.

FIELD OF THE INVENTION

The present subject matter relates to an efficient method for collecting placenta cord blood stem cells, an easy method for safe long duration cold storage of the placenta, and methods for using the collected stem cells.

BACKGROUND OF THE INVENTION

1. Field of the Invention

The present subject matter relates to stem cell collection from the placenta detailing a new method which is clinically feasible, convenient, and highly efficient. It also involves making harvesting and banking of all tissues derived from the placenta easy, efficient, under the highest quality control by delivering the clamped unmanipulated cooled sterile packaged placenta post-partum to a potential centralized facility that can service a local, state, country, region, or world-wide customer/patient base. Particularly, the present subject matter describes a new finding that residual placenta cord blood cells gathered by machine pulsatile perfusion are more enriched with the primitive hematopoietic stem cell phenotypes (CD133+) compared to those from conventional needle/syringe withdrawal or gravity drainage collection and potentially allows cord blood cells from a single donor to be used for regenerative medicine purposes through out a lifetime. Increased stem cell numbers obtained from a single placenta using the described method can also improve allogeneic hematopoietic stem cell transplant outcomes and obviate the use of double or triple cord blood grafts from different donors in order to compensate for insufficient stem cells from a single donor graft. Another particular of the present subject matter is the new finding that a whole unmanipulated placenta right after delivery with the umbilical cord clamped can be placed into a suitable sterile container that is cooled with ice and transported to a central facility up to 40 hours away for harvesting and banking of all available tissue types without any significant loss of viability.

2. Description of the Background Art

Cord Blood Collection Method and Cord Blood Transplantation in Adults

Umbilical CB cells are a promising source of HSC to perform allogeneic HSC transplantation for hematological malignancies and bone marrow failure syndrome (Kurtzberg et al., 1996; Wagner et al. 1996; Gluckman et al., 1997; Rubinstein et al., 1998). Significant advantages include a rapid access to CB cells which are stored in CB banks nationwide and acceptance of 1-2 human leukocyte antigen mismatch grafts due to infrequent severe graft versus host disease (GVHD) compared to the matched unrelated donor grafts (Barker et al. 2002). CB cells enable patients to choose allogeneic transplant as a curative option for hematological malignancies where otherwise no suitable match donors are available, particularly among patients in minority groups. Despite the above advantages, the use of CB is limited in adults due to insufficient numbers of cells, including CD34+ cells and progenitors. CB transplant using low levels of total nucleated cell counts leads to significant delays in post-transplant engraftment of neutrophils and platelets or engraftment failures (Wagner et al., 2002; Laughlin et al. 2004). Known procedures for harvesting CB include draining the blood by gravity from the delivered placenta, and draining the blood by venipuncture into collection bags or syringes.

Since CB supplies are barely enough for only one time use or more recently using double CB supplies from two non-identical donors, adult CB transplants have been performed generally under a clinical research basis only when suitable unrelated donors are not available. In practice, a recovery of only 20-40 ml is not unusual and these CB cells are therefore not even used or stored (Lasky et al., 2002; George et al., 2006). In such cases, a significant amount of uncollected CB cells still remain in the placenta and are discarded since there is no standardized supplemental method that can collect them after the initial harvest to supplement it. To expand the future CB bank donor pool, it is important to investigate improved CB harvesting methods including how to collect the residual CB cells that are left after conventional CB harvesting (Harris et al., 1994). More importantly, availability of an increased amount of CB cells from the same placenta may allow storing an amount of CB cells sufficient for multiple uses including back up or graft engineering such as an ex vivo expansion and adoptive immunotherapy.

Current Knowledge in HSC Plasticity and Tissue Regeneration

Over the past decade, many types of stem cells which have the capacity to replicate, self-renew, and differentiate, have been identified in humans. Totipotent stem cells are capable of forming every type of body cell, and these cells are within the early embryo and are the so-called human ES cells. Pluripotent stem cells are capable of developing into endoderm, mesoderm, or ectoderm. Tissue specific stem cells are committed to make certain tissues only. For example, hematopoietic stem cells (HSC) are responsible for all types of blood cells but no other tissue types and their continued presence in an adult allows for a repair capability. However, investigators have found that cells like adult HSC which were considered to be responsible for production of different types of hematopoietic progenitor cells even gave rise to cells of different tissue or organ such as neural cells or muscle cells.

Research studies on transdifferentiation of adult HSC continue to be controversial and active research investigations are on going. In contrast, a number of clinical cases have reported evidence of nonhematopoietic cell generation after either BM transplantation or cardiac transplantation. A retrospective study to look for BM transdifferentiation into brain after BM transplantation showed evidence of neuropoiesis, detection of astrocytes and microglia in a long-term setting without cell fusion (Cogle et al. 2004). Other reports have noted detection of donor cells in osteoblasts, hepatocytes, gastro-intestinal (GI) tract epithelia, stroma after BM transplant; keratinocytes/hepatocytes/GI tract/skin epithelia after peripheral blood stem cell transplant; and cardiomyocytes with and without endothelium after cardiac transplant with a wide range of percent amounts found (Hruban et al., 1993; Theise et al., 2000; Korbling et al., 2002; Muller et al., 2002; Okamoto et al., 2002; Quaini et al., 2002).

Cord Blood Cells as a Source of Adult Stem Cells

Although human ES cells can be differentiated and expanded in vitro to produce different types of progenitors, its application in patients is currently hindered by multiple ethical issues. In addition, the purity issue of embryonic stem cell-derived progenitor cells has to be solved. By contrast, adult stem cell populations derived from hematopoietic tissues including bone marrow and umbilical CB cells were found to be capable of differentiation into ectoderm or endoderm upon exposure to adequate stimuli (Eglitis and Mezey, 1997; Brazelton et al., 2000; Mezey et al., 2000; Sanchez-Ramos et al. 2001; Chen et al. 2005). In particular, CB derived stem cells have further advantages compared to the other sources since they are collected from the placenta which is normally discarded, thus requiring no tissue damage to the host upon harvesting the cells. Compared to the BM cells, CB has primitive ontogeny with naïve immune status and relatively unshortened telomere length.

Among debates concerning whether truly pluripotent somatic stem cells exist, cells derived from the CB and placenta have been increasingly focused on as containing interesting properties for potential clinical exploitation. Recently, CB has been shown to contain a heterogeneous cell population and recognized as a source of pluripotent stem cells (Goodwin et al., 2001; Sanchez-Ramos et al., 2001; Bicknese et al. 2002; Sanchez-Ramos, 2002; Zigova et al., 2002) Others reported that adherent cell population isolated from a week long suspension culture of CB cells after lineage positive cell depletion were shown to express immunohistochemical evidence of ectodermal and endodermal features (McGuckin et al., 2004). There is a series of successful CB transplant reports on children suffering from the neurodegenerative disorder Krabbe leukodystrophy (Escolar et al., 2005).

The present inventor hypothesizes that these unique features found in CB stem cells may be from a recently published emerging concept that the gestational placenta may be a hematopoietic niche during embryo development (Gekas et al., 2005; Ottersbach and Dzierzak, 2005). It is a simple assumption that a full-term placenta may also contain remnant primitive stem cells adherent to the vascular niche, or possibly due to the stress associated with "birth", there may be an increased number of circulating stem cells that are released from fetal BM or liver which have migrated to the placenta niche. Thus, the present inventor hypothesizes that placenta derived CB cells obtained by this innovation may contain more primitive stem cells (ES cell-like cells) left as remnant stem cells deposited in a placenta vascular bed niche since embryogenesis.

Isolation and Selection of Primitive CB Cells Including ES Cell-Like Cells and Primitive HSC To identify common stem cell markers using comparison analysis of gene expression patterns from embryonic, hematopoietic, and neural stem cells, only one gene was identified (probably due to technical difficulties) (Fortunel et al. 2003). Thus, to identify and select stem cells may still require several markers to isolate these cells. One of the characteristics that can be used to distinguish stem cells is the absence of markers of differentiation. This approach has been used widely in HSC field to perform enrichment of stem cells to be employed for therapy. This "Lineage negative (Lin−)" trait is a common property of many stem cell populations (Cai et al., 2004b). To further enrich the stem cell population from Lin− CB cells, it has been reported that CD133+ marker demonstrated a high proliferation potential on growth factor stimulation (Forraz et al., 2004). Others reported that CD133+/CD34− subset might represent more primitive stem cells as they did not produce colony forming cells (CFC) in methylcellulose, but exhibited the highest SCID repopulating cells frequency (Kuci et al., 2003). Embryonic stem cell markers such as stage-specific embryonic antigen (SSEA)-3, SSEA-4, TRA-1-60, and TRA-1-81 are expressed only on ES cells which have been widely used in the characterization of pluripotent stem cell and antibodies compatible to FACS analysis (which are commercially available). Most recently, Kucia et al. described a primitive stem cell population called "very small embryonic-like (VSEL) stem cells" which carry Lin−/CD45−/CXCR4+/CD133+/CD34+ phenotype (Kucia et al. 2006). These cells were also positive for embryonic transcription factors Oct-4 and Nanog.

Alternatively, the method using the presence of general metabolic markers has also been used to identify and isolate stem cells. One of the metabolic markers that has been described is aldehyde dehydrogenase (ALDH) (Takebe et al., 2001). The fluorescent substrate of ALDH, Aldefluor (StemCell), has been used to demonstrate increased ALDH activity in neural stem cells (Cai et al., 2004b; Corti et al., 2006) and HSC (Storms et al. 1999). This nontoxic, live labeling method can be used to identify other stem cell populations as well (Cai et al., 2004a). Furthermore, Rhodamine uptake and Hoechst dye labeling has been used to select stem cell populations from BM, CB, mesenchymal, muscle, and adult brain (Kim et al., 2002; Bhattacharya et al., 2003; Migishima et al., 2003; Parmar et al., 2003). The side population (SP) which is demonstrated by low uptake of Hoechst dye 33342 represents the highest capability of self-renewing and pluripotency. Hoechst dye uptake is regulated by a membrane transporter ABCG2 and the SP population is defined as the expression of ABCG2 protein (Zhou et al., 2001; Scharenberg et al., 2002). ABCG2 protein is also expressed specifically in neural stem cells and decreases in expression when precursor cells differentiate (Cai et al., 2002).

Evidence of Ectodermal Cell Transdifferentiation from Human Hematopoietic Cell Lineage.

There are increasing reports of BM stroma derived progenitors differentiating into neural cells since these cells were first reported to show differentiation into muscle, glia, and hepatocytes in mouse (Azizi et al., 1998; Ferrari et al., 1998; Petersen et al., 1999). In vitro evidence of neuron specific proteins inductions, such as nestin, neuron-specific nuclear protein (NeuN), and glial acidic fibrillary protein (GFAP) in cells derived from human and rodent BM stromal cells were reported after stimulation with retinoic acid, epidermal growth factor (EGF), or brain derived neurotrophic factor (BDNF) (Sanchez-Ramos et al., 2000). Among non-mesenchymal hematopoietic progenitors, several reports have shown that human CB mononuclear cells including separated CD133+ cells were induced to express neuronal and glial markers in vitro such as beta-tublin III, GFAP after exposure to basic fibroblast growth factor (bFGF) and hEGF, and also Musashi-1 after retinoic acid and nerve growth factor (NGF) exposure (Sanchez-Ramos et al. 2001; Bicknese et al., 2002).

Evidence of Endodermal Cell Transdifferentiation from Hematopoietic Cell Lineage.

Previously, hepatocytes were thought to be transformed from infused BM cells in a mouse model (Lagasse et al., 2000), but it was found to be caused by cell fusion in that particular liver regeneration model (Wang et al., 2003b). Others also found that myelomonocytic cells from BM HSC source were the major source of hepatocyte fusion partners (Camargo et al., 2004). CB cells isolated from a lineage positive cell depletion procedure followed by a week of suspension culture formed an adherent cell population which were found to express markers for hepatic cells after further incubation with hepatocyte growth medium (McGuckin et al., 2005). In vivo evidence of hepatocyte-like cell development in the liver treated with $CCl_4$ in immune deficient mice after CB CD34+CD38−CD7− transplant was reported (Wang et al., 2003a) and more recently in a non-injury model using fetal sheep, human hepatocytes were generated through BM reconstitution of fetal sheep by human HSC, including CD34+/Lin−, CD34−/Lin−, CD34+/Lin−/CD38−, CD34−/

Lin−/CD38−, CD34+/Lin−/CD133+, CD34+/Lin−/CD133− derived from either BM, peripheral blood, or CB (Almeida-Porada et al., 2004).

Harvesting and Banking of Other Tissue Types from the Placenta.

The placenta as a valuable source of a wide variety of tissues (other than cord blood) that can be harvested, banked, and transplanted has been gaining increasing acceptance within the medical community (Parolini et al., 2008). For example, a part of the placenta called the amnion, or the outer membrane of the amniotic sac, is comprised of cells that have strikingly similar characteristics to embryonic stem cells, including the ability to express two key genes that give embryonic stem cells their unique capability for developing into any kind of specialized cell. Amniotic epithelial cells could in fact be directed to form liver, pancreas, heart and nerve cells under the right laboratory conditions. Another example is Wharton's Jelly composed of primitive connective tissue of the umbilical cord. Wharton's jelly stem cells (WJSCs) have significant therapeutic potential because large number of cells are easily isolated and may be better tolerated following transplantation because of their low immunogenicity and immune suppression. The cells are a potential important tool for tissue engineering, cell and gene therapy for various genetic diseases and acquired diseases since WJSCs can be induced to form adipose tissue, bone, cartilage, skeletal muscle, cardio myocyte-like cells and neural cells. WJSCs could be used to treat protein deficiencies, disorders of bone and cartilage, cardiac diseases, bone marrow stromal disorders, neurological diseases such as Parkinson's disease, multiple sclerosis, cerebrovascular accidents (stroke) and even cerebral palsy. Finally, placental tissues have been used directly in the treatment of burned and ulcerated skin and conjunctival defects. It is noted that amniotic membranes have many beneficial properties including anti-inflammatory, bacteriostatic, analgesia, wound healing, etc.

SUMMARY OF THE INVENTION

The present subject matter relates to an innovative method of collecting cord blood (CB) derived stem cells from a placenta, an easy method for safe long duration cold transportation of the placenta for comprehensive tissue harvesting and banking at a centralized facility within 40 hours of the post-partum delivery, and methods for using the collected stem cells. In one embodiment of the invention, the placental perfusion may be performed by pulsatile machine placental perfusion (PMPP). PMPP can be combined with either completion of a conventional collection method, usually venipuncture (aspiration of umbilical cord vasculature with a needle and syringe) or gravity drainage, or no prior collection. PMPP can be performed with an anticoagulant containing organ perfusion solution to flush the cord blood cells out and subsequently collect the resulting stem cell containing perfusate. This method does not require any preparation or injection of anticoagulants into the placenta post delivery to prevent clotting. The isolated placenta can be cooled, for example, by placing on ice, prior to perfusion. If perfusion is performed within one hour of placental isolation, the placenta need not be cooled prior to perfusion. The presently described method may still be performed if the placenta is prepared or injected with an anticoagulant prior to performing perfusion. If cord blood cells are first collected using conventional methods, the residual cord blood cells obtained with PMPP can be added to this initial collection. The PMPP obtained cord blood cells can also be stored as back up cells or stored for future cell graft engineering and regenerative medicine purposes. The convenience of not needing immediate removal of cord blood stem cells from the placenta and the ability to ship it directly on ice only without any further preparations to a central facility makes this method potentially attractive to be incorporated into the currently established cord blood cell banking system by transportation of the placenta for comprehensive tissue harvesting and banking at a centralized facility (for local, state, country, regional, continent, world-wide customer/patient base)

One embodiment comprises a method of collecting cord blood stem cells from an isolated non-exsanguinated or partially exsanguinated mammalian placenta. Other embodiments can comprise performing placental perfusion on a mammalian placenta with a perfusion solution, for example, at least a first volume of perfusion solution, to produce a perfusate comprising cord blood stem cells; collecting the perfusate comprising cord blood stem cells; and isolating cord blood stem cells from the perfusate to produce isolated cord blood stem cells. Perfusing can comprise perfusing with one or more volumes of perfusion solution, for example, from 1 to 3 volumes of perfusion solution.

In some embodiments, the perfusing comprises subjecting the non-exsanguinated or partially exsanguinated mammalian placenta to a pressure-mediated flow of perfusion solution. In certain embodiments, pressure-mediated flow of perfusion solution comprises a pulsatile flow of perfusion solution. In some embodiments the pressure-mediated flow of perfusion solution comprises one or more of a positive pressure-mediated flow of perfusion solution or a negative pressure-mediated flow of perfusion solution.

In some embodiments, the method comprises subjecting the non-exsanguinated or partially exsanguinated mammalian placenta to a pressure-mediated flow of perfusate, for example, via pulsatile perfusion, wherein perfusing is carried out under conditions sufficient to produce a mammalian placenta substantially free from cord blood stem cells. It is also substantially free to totally free of all intravascular blood ensuring cross contamination of other harvested placental tissues by blood is minimized. In further embodiments, the placental perfusion is performed using a peristaltic pump.

Generally, the method involves isolating stem cells present in the cord blood of an isolated placenta. The isolated stem cells may comprise embryonic stem cell (ES)-like stem cells, hematopoietic stem cells, mesenchymal stem cells or combinations thereof. Other cord blood cells that can be obtained by this method include T-cells, monocytes, dendritic cells, and B cells.

In other embodiments, the method may further comprise: prior to perfusing, isolating a mammalian placenta from a mammalian donor to produce an isolated mammalian placenta; and cooling the isolated mammalian placenta to produce a cooled mammalian placenta.

In several embodiments, the isolated placenta is cooled or kept on ice after procurement, and before perfusing. In some embodiments, the cooled isolated placenta is maintained at a temperature ranging from about >0° C. to about 6° C., or from about 1° C. to about 4° C., provided the placenta is not permitted to freeze, prior to performing the perfusion. In other embodiments, the placenta is maintained at a temperature ranging from about 4° C. to about 10° C. for four hours, prior to performing the perfusion. In one embodiment, the placenta is kept at 4°, prior to performing the perfusion. In certain embodiments, the isolated cooled placenta is maintained for a period of time of up to about 40 hours, after procurement and before perfusing, facilitating comprehensive harvesting of other placenta derived tissue types and banking at a centralized facility within 40 hours of the post-partum delivery.

In some embodiments, the method does not require administration or injection of an anticoagulant into the placenta prior to perfusing. In one embodiment, the placenta is not administered or injected with an anticoagulant prior to perfusing.

In some embodiments, the perfusate solution comprises a physiologically-compatible solution Belzer (non-human use RPMI of IMDM). In other embodiments, the perfusate solution comprises an anticoagulant. In certain embodiments, the perfusate solution comprises an anticoagulant selected from heparin, creatine phosphate dextrose (CPDA), or any combination of two or more thereof.

In some embodiments, the placenta is partially exsanguinated prior to performing placental perfusion. Generally, the cord blood may be exsanguinated from the placenta using standard methods such as venipuncture (for example, by needle and syringe) or gravity drainage (for example, by needle and bag). Generally, stem cells may be isolated from the cord blood exsanguinated from the placenta by such standard methods. In some embodiments of the invention, stem cells isolated from the exsanguinated placenta using standard methods may be combined with stem cells isolated using the inventive perfusion methods. In some embodiments, the combined stem cells from both methods may be used to derive further stem cell ontogeny.

In one embodiment, the placenta is perfused via a closed system using the umbilical arteries and/or umbilical vein. In some embodiments, the placenta is perfused, and the cord blood removed comprising viable stem cells, up to about 40 hours post-delivery which allows for centralized harvesting and banking at a facility serving a large geographic area up to an including world-wide. In certain embodiments, the placenta is perfused, and the cord blood removed comprising viable stem cells, between about 6 hours and about 40 hours post-delivery.

In some embodiments, the PMPP of the attached placenta is performed at a pulse setting of about 15-60 beats/min. In certain embodiments, the PMPP of the attached placenta is performed at a systolic pressure ranging from 15 to 70 mmHg. In yet further embodiments, the PMPP of the attached placenta is performed for a time ranging from 5 min to 90 min, during which time cord blood is removed from the placenta. In some embodiments, the PMPP of the attached placenta is performed for a time ranging from 15 min to 35 min. In other embodiments, the PMPP of the attached placenta is performed for a time ranging from 20 min to 30 min. In further embodiments, the PMPP of the attached placenta is performed for a minimum amount of time selected from at least 10 min, at least 15 min, at least 20 min, at least 25 min, at least 30 min, at least 40 min, at least 50 min, and at least 60 min, wherein the maximum perfusion time is not greater than 90 minutes for the selected minimum amount of time.

In certain embodiments, the isolated primitive hematopoietic stem cell phenotypes comprise one or more of CD133+ cells, CD34+/CD38− cells, CD133+/CD34+ cells, CD133+/CD34− cells, CD117+ cells, CD90+ cells, CD59+ cells, Thy1+ cells, Lin− cells, CXCR4+ cells, ALDH$^{high}$ cells, side population (SP) cells, SSEA-3+ cells, SSEA-4+ cells, TRA-1-60 cells, TRA-1-81 cells, or combinations thereof. In further embodiments, the isolated stem cells comprise primitive hematopoietic stem cell phenotypes that can differentiate into cells other than CD34+/CD38− cells, CD133+ cells, CD133+/CD34+ cells, or CD133+/CD34− cells.

In one embodiment, a method of collecting cord blood stem cells is described that can comprise or consist of providing an isolated non-exsanguinated or partially exsanguinated mammalian placenta comprising cord blood comprising cord blood stem cells; perfusing the an isolated non-exsanguinated or partially exsanguinated mammalian placenta with a pressure mediated flow of a perfusion solution to produce a perfusate comprising cord blood comprising cord blood stem cells; collecting the perfusate; and isolating the cord blood stem cells from the perfusate to produce isolated cord blood stem cells. The isolated cord blood stem cells can be cryopreserved.

In another embodiment, a method of collecting cord blood stem cells is described that can comprise or consist of providing an isolated non-exsanguinated mammalian placenta comprising cord blood comprising cord blood stem cells; partially exsanguinating the isolated non-exsanguinated mammalian placenta to produce a partially exsancuinated placenta and a volume of cord blood comprising cord blood stem cells; perfusing the partially exsanguinated mammalian placenta with a pressure mediated flow of a perfusion solution to produce a perfusate comprising cord blood comprising cord blood stem cells; collecting the perfusate; and isolating the cord blood stem cells from the volume of cord blood and from the perfusate to produce isolated cord blood stem cells. The isolated cord blood stem cells can be cryopreserved.

In some embodiments, the PMPP perfusate plus aspiration of cord blood from the umbilical vasculature with a conventional exsanguination method, such as a needle and syringe, results in about a 1.5-fold increase total mononuclear cell count obtained from one placenta compared to aspiration of cord blood from the umbilical vasculature with a needle and syringe alone. A comparable total cell recovery is possible if the placenta is not exsanguinated prior to performing the inventive perfusion method.

In a further embodiment, wherein the PMPP perfusate plus aspiration of cord blood from the umbilical vasculature with a conventional exsanguination method, such as a needle and syringe, results in about a 5-fold enriched CD133+ cell percentage obtained compared to aspiration of cord blood from the umbilical vasculature with a needle and syringe alone. A comparable total cell recovery is possible if the placenta is not exsanguinated prior to performing the inventive perfusion method.

In yet another embodiment, the PMPP perfusate plus aspiration of cord blood from the umbilical vasculature with a conventional exsanguination method, such as a needle and syringe, results in about a 7-fold higher CD133+ cell population obtained compared to aspiration of cord blood from the umbilical vasculature with a needle and syringe alone. A comparable total cell recovery is possible if the placenta is not exsanguinated prior to performing the inventive perfusion method.

In one embodiment, the PMPP perfusate plus aspiration of cord blood from the umbilical vasculature with a conventional exsanguination method, such as a needle and syringe, results in about a 5.5 fold increased percentage of CD34+ cells obtained compared to aspiration of cord blood from the umbilical vasculature with a needle and syringe alone. A comparable total cell recovery is possible if the placenta is not exsanguinated prior to performing the inventive perfusion method.

In another embodiment, the PMPP perfusate plus aspiration of cord blood from the umbilical vasculature with a conventional exsanguination method, such as a needle and syringe, results in about a 4.9-fold increased total CD34+ cells obtained compared to aspiration of cord blood from the umbilical vasculature with a needle and syringe alone. A comparable total cell recovery is possible if the placenta is not exsanguinated prior to performing the inventive perfusion method.

In yet another embodiment, the PMPP perfusate plus aspiration of cord blood from the umbilical vasculature with a conventional exsanguination method, such as a needle and syringe, results in about a 14.8-fold increased CD34+/CD38– cell population percentage obtained compared to aspiration of cord blood from the umbilical vasculature with a needle and syringe alone. A comparable total cell recovery is possible if the placenta is not exsanguinated prior to performing the inventive perfusion method.

In yet another embodiment, the PMPP perfusate plus aspiration of cord blood from the umbilical vasculature with a conventional exsanguination method, such as a needle and syringe, results in about an 11 times more CD34+/CD38– cells being collected compared to aspiration of cord blood from the umbilical vasculature with a needle and syringe alone. A comparable total cell recovery is possible if the placenta is not exsanguinated prior to performing the inventive perfusion method.

In other embodiments, the cord blood stem cells may be cryopreserved.

In some embodiments, the described subject matter includes a method for treating a mammal (any species including horses) in need of hematopoietic reconstitution comprising (a) isolating hematopoietic stem cells derived from placental cord blood according to a method described herein and (b) culturing in vitro the hematopoietic stem cells isolated according to a method described herein, thereby producing progeny stem cells. In certain embodiments, these progeny stem cells may be used immediately or stored, for example by cryopreservation, for future use, such as in a unit for delivery to a patient in need thereof. In further embodiments, the method may further comprise (c) introducing into the mammal a composition comprising a therapeutically effective amount of the progeny stem cells, whereby hematopoietic reconstitution is effected. In some embodiments, the mammal is chosen from a human or a primate, for example, such as a baboon or other primate.

In other embodiments, the described subject matter includes a method for treating a mammal in need of hematopoietic reconstitution comprising (a) isolating hematopoietic stem cells derived from placental cord blood according to a method described herein and (b) introducing into the mammal a composition comprising a therapeutically effective amount of the isolated hematopoietic stem cells, whereby hematopoietic reconstitution is effected. In some embodiments, the mammal is chosen from a human or a primate, for example, such as a baboon or other primate.

In additional embodiments, the method for treating a mammal in need of hematopoietic reconstitution may further comprise cryopreserving the isolated stem cells before they, or their derived progeny cells, are introduced into a mammal in need thereof. In further embodiments, the isolated stem cells, or their derived progeny cells, that are introduced into a mammal in need thereof may be allogeneic, autologous, or a combination thereof, to the mammal receiving the cells. In certain embodiments, the isolated stem cells from more than one placenta can be pooled together for use in treating a mammal in need thereof. In further embodiments, the progeny derived from isolated stem cells of one isolated placenta can be pooled together with progeny derived from one or more additional isolated placentas for use in treating a mammal in need thereof.

In some embodiments, the method for treating a mammal in need of hematopoietic reconstitution involves a mammal that has aplastic anemia, a hematopoietic malignancy, an autoimmune disease, a genetic disorder, an immunodeficiency, a malignant solid tumor, or a combination thereof.

In certain embodiments, the mammal in need of hematopoietic reconstitution has a hematopoietic malignancy selected from leukemia, lymphoma, multiple myeloma, myelodysplastic syndrome. In further embodiments, the mammal in need of hematopoietic reconstitution has an immunodeficiency resulting from irradiation, chemotherapy, infection by a pathogenic microorganism, or a combination thereof.

In an embodiment, the described subject matter includes a method for regenerating damaged tissue in a mammal in need thereof, comprising: (a) culturing in vitro the cord blood stem cells isolated according to claim 1, thereby producing differentiated cells or expanded stem cells; and (b) introducing into the mammal intravenously or direct injection into the target organ a composition comprising a therapeutically effective amount of the differentiated cells or expanded stem cells, whereby tissue regeneration is effected. In a further embodiment, a method is described for regenerating damaged tissue in a mammal in need thereof, comprising introducing into the mammal intravenously or direct injection into the target organ a composition comprising a therapeutically effective amount of the cord blood stem cells isolated according to claim 1, whereby tissue regeneration is effected.

In other embodiments, a method is described for regenerating damaged tissue in a mammal in need thereof, wherein the tissue comprises one or more of cardiac tissue, muscle tissue, liver tissue, skin, neural tissue, bone tissue, epithelia, stroma, or endothelium.

BRIEF DESCRIPTION OF THE FIGURES

In the detailed description of the invention presented below, reference is made to the accompanying drawings in which:

(FIG. 1) Raw data is presented in Table 3.

Figure 1:
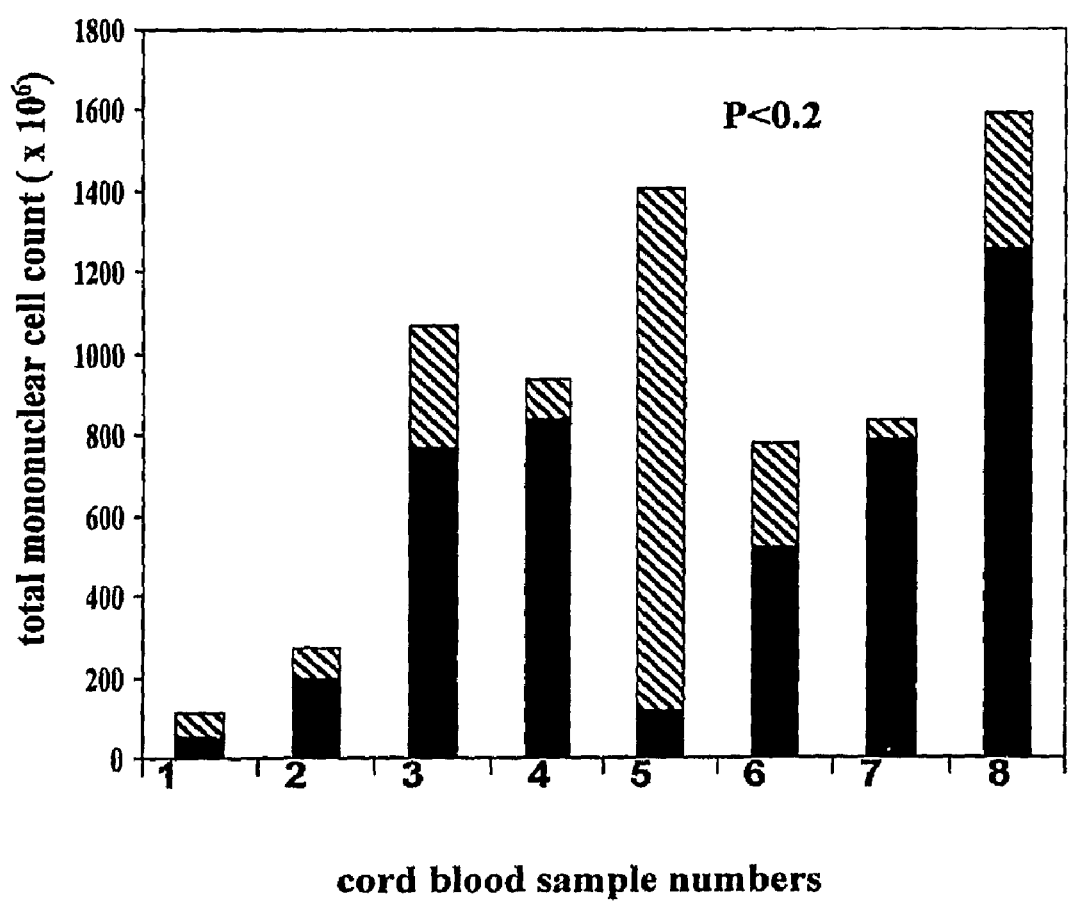
FIG. 1. Pulsatile machine placenta perfusion (PMPP) enables 1.5-fold increase total mononuclear cell count per placenta (venipuncture fraction plus PMPP fraction) compared to venipuncture alone. The figure represents an analysis of 8 placenta derived CB samples obtained by venipuncture method (solid black) followed by machine placenta perfusion method (stripe pattern). Arabic numbers below each bar represent the sample numbers displayed in the Table 1.
Figure 2:
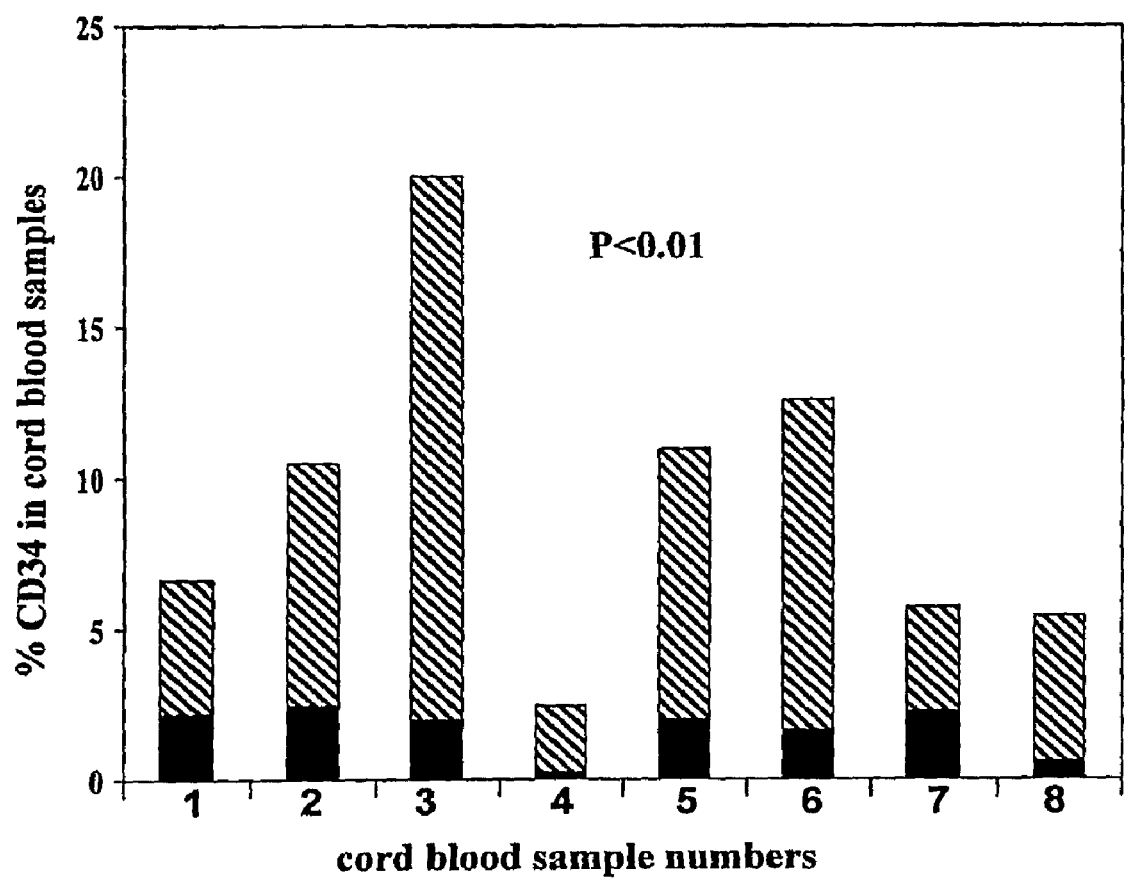
FIG. 2. Percentage of CD34+ cell fraction obtained via PMPP method contained 4.9-fold increased percentage compared to that from the venipuncture fraction.
Figure 3:
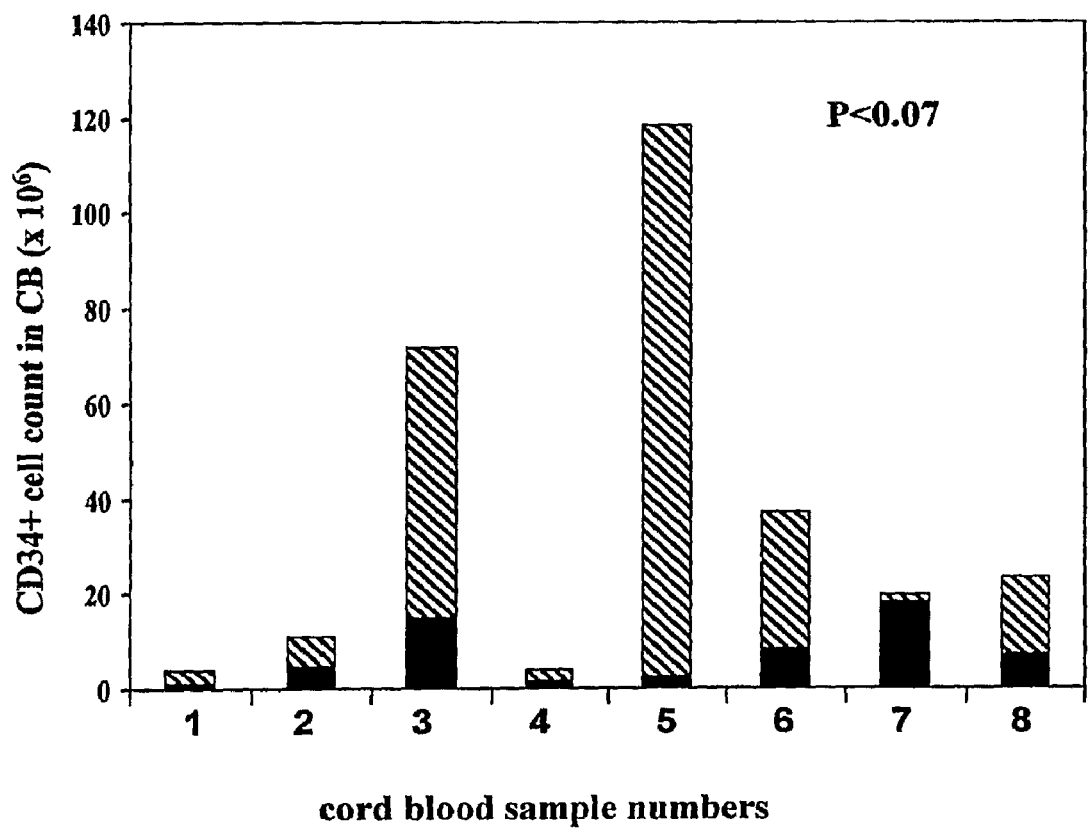
FIG. 3. CD34+ cell count from venipuncture fraction and PMPP fraction was $7.4 \times 10^6 \pm 5.9 \times 10^6$ (mean±S.D.) (range of 8 patients, $1.1-18.2 \times 10^6$) and $28.8 \times 10^6 \pm 37 \times 10^6$ (mean±S.D.) (range $1.6-116 \times 10^6$), respectively, indicating that PMPP fraction contained a 3.9-fold increased total CD34+ cells.
Figure 4:
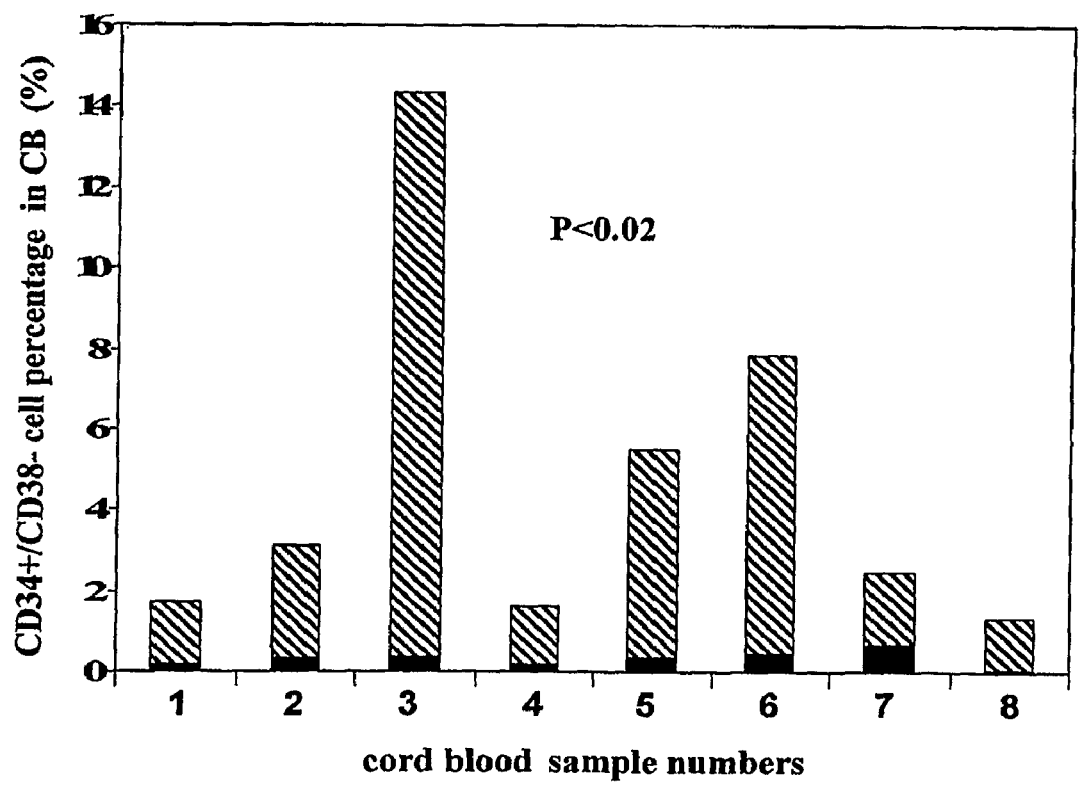
FIG. 4. The mean percentage of CD34+/CD38– cells in venipuncture and PMPP fractions was 0.32±0.17% (mean±S.D.) (range 0.04-0.66) and 4.4±4.1% (mean±S.D.) (range 1.3-14), respectively demonstrating that PMPP fraction contained a 13-14-fold increased CD34+/CD38– cell population percentage compared to venipuncture fraction.
Figure 5:
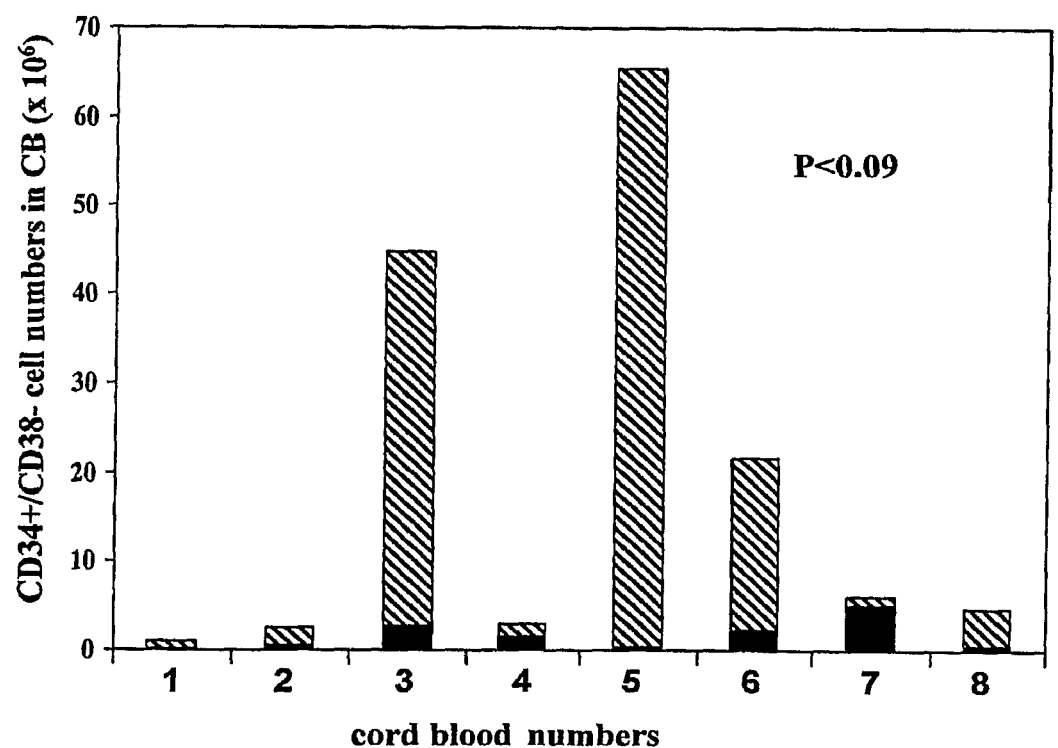
FIG. 5. The absolute number of CD34+/CD38– cells in venipuncture and PMPP fraction was $1.7 \pm 1.5 \times 10^6$ (mean±S.D.) (range 0.12-5.2) and $17 \pm 22 \times 10^6$ (mean±S.D.)

(range 0.86-65), respectively (FIG. 5), indicating that PMPP fraction contained 10 times more CD34+/CD38− cells.

Figure 6:
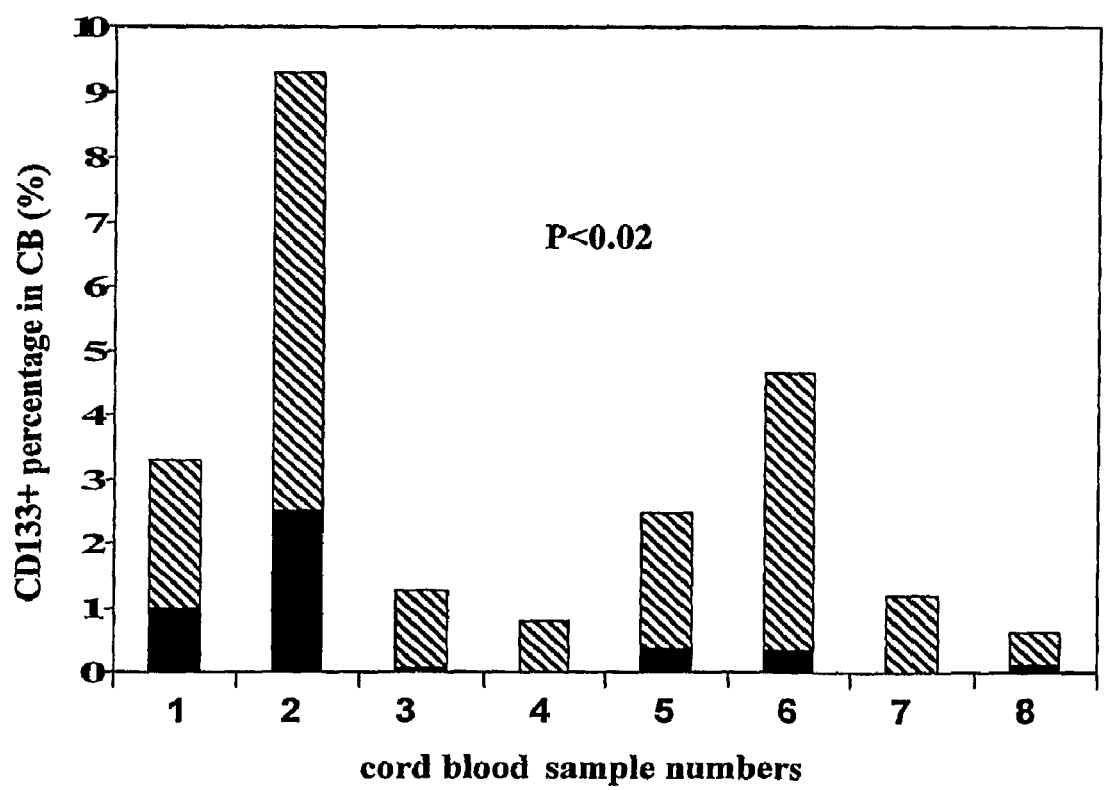

FIG. 6. CD133+ cell percentage in venipuncture and PMPP fraction was 0.55±0.8% (mean±S.D.) (range 0-2.5) and 2.4±2.0% (mean±S.D.) (range 0.5-6.8) respectively, demonstrating a 4-fold enriched CD133+ cell percentage in PMPP fraction.

Figure 7:
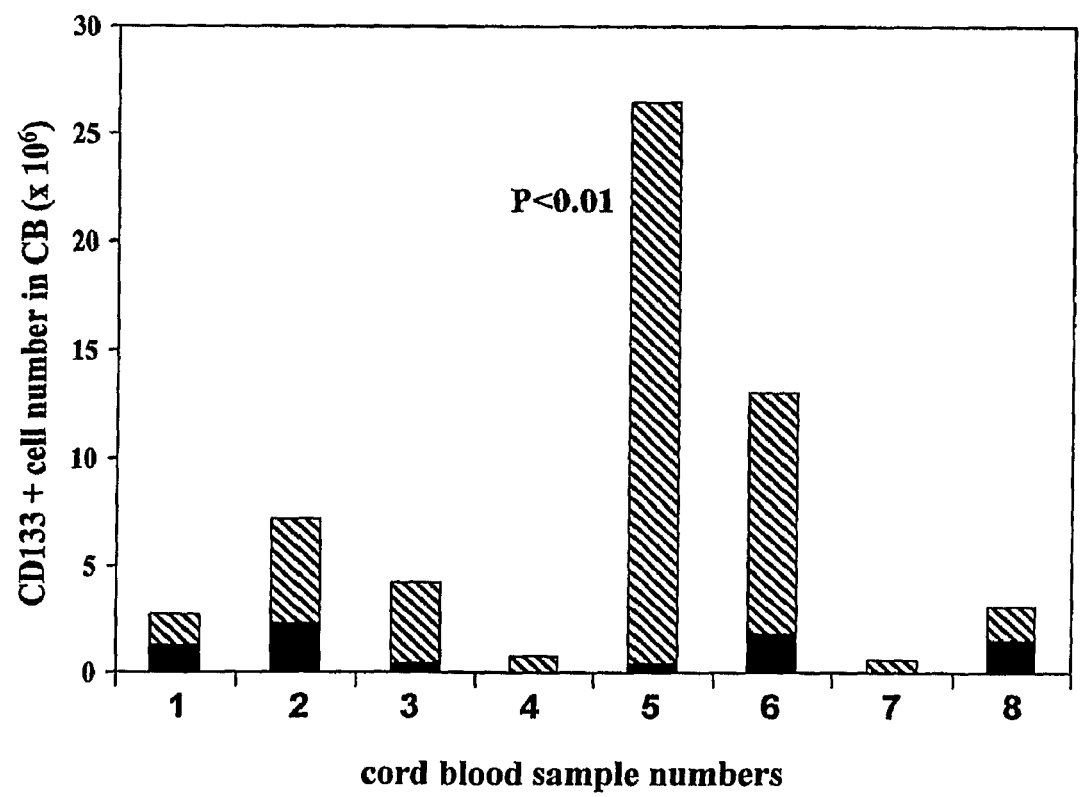

FIG. 7. CD133+ cell number in venipuncture and PMPP fraction was 0.98±0.8×10$^6$ (mean±S.D.) (range 0-2.3) and 6.3±0.8×10$^6$ (mean±S.D.) (range 0.55-11.2), respectively. CD133+ cell population in PMPP fraction was significantly enriched at a 6.3-fold higher level.

Figure 8A:
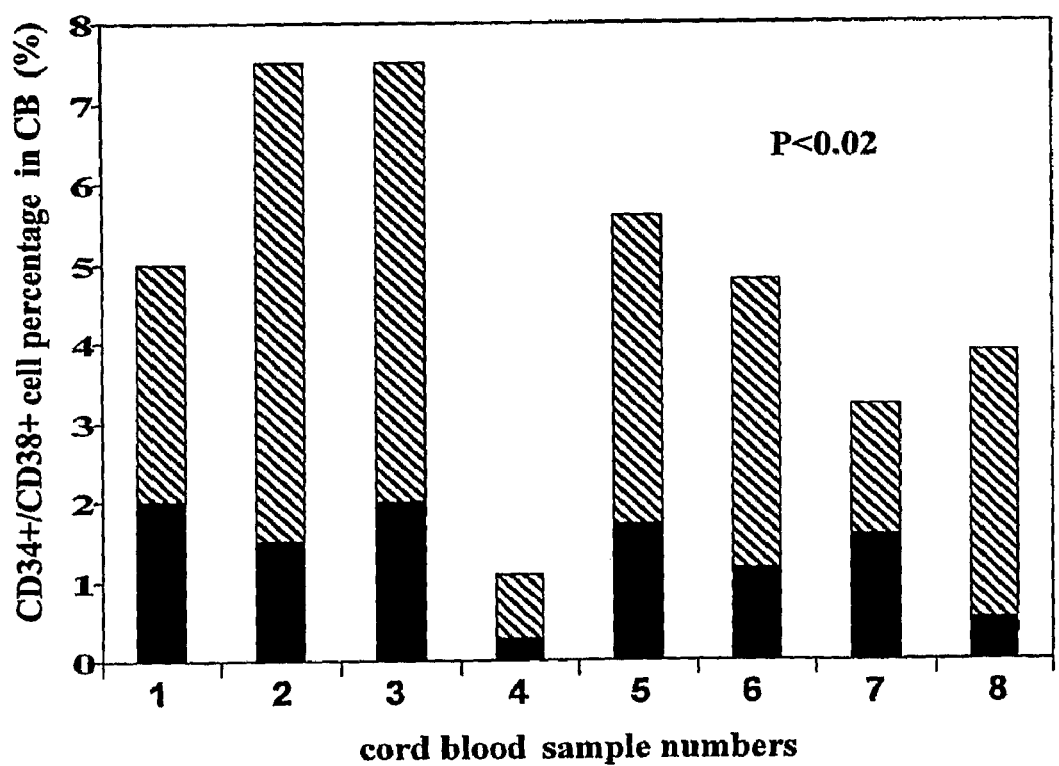
Figure 8B:
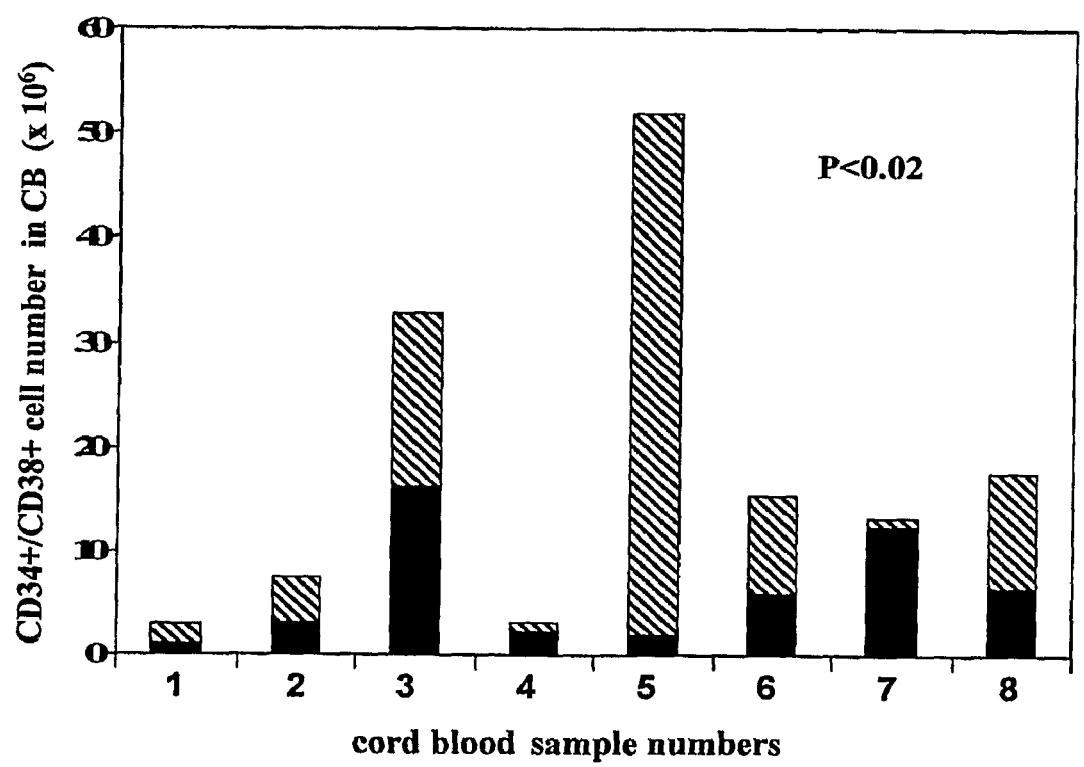

FIGS. 8A and 8B. The mean percentage and absolute number of CD34+/CD38+ cells in venipuncture and PMPP fractions was 1.34±0.6% (mean±S.D.) (range 0.26-2), 6.1±5.1×10$^6$ (mean±S.D.) (range 1.0-16.2), and 3.5±1.6% (mean±S.D.) (range 0.82-6), 11.9±15×10$^6$ (mean±S.D.) (range 0.78-50), respectively, demonstrating a 2.6-fold and 1.95-fold increase CD34+/CD38+ percentage and absolute number, respectively, favoring PMPP.

Figure 9A:
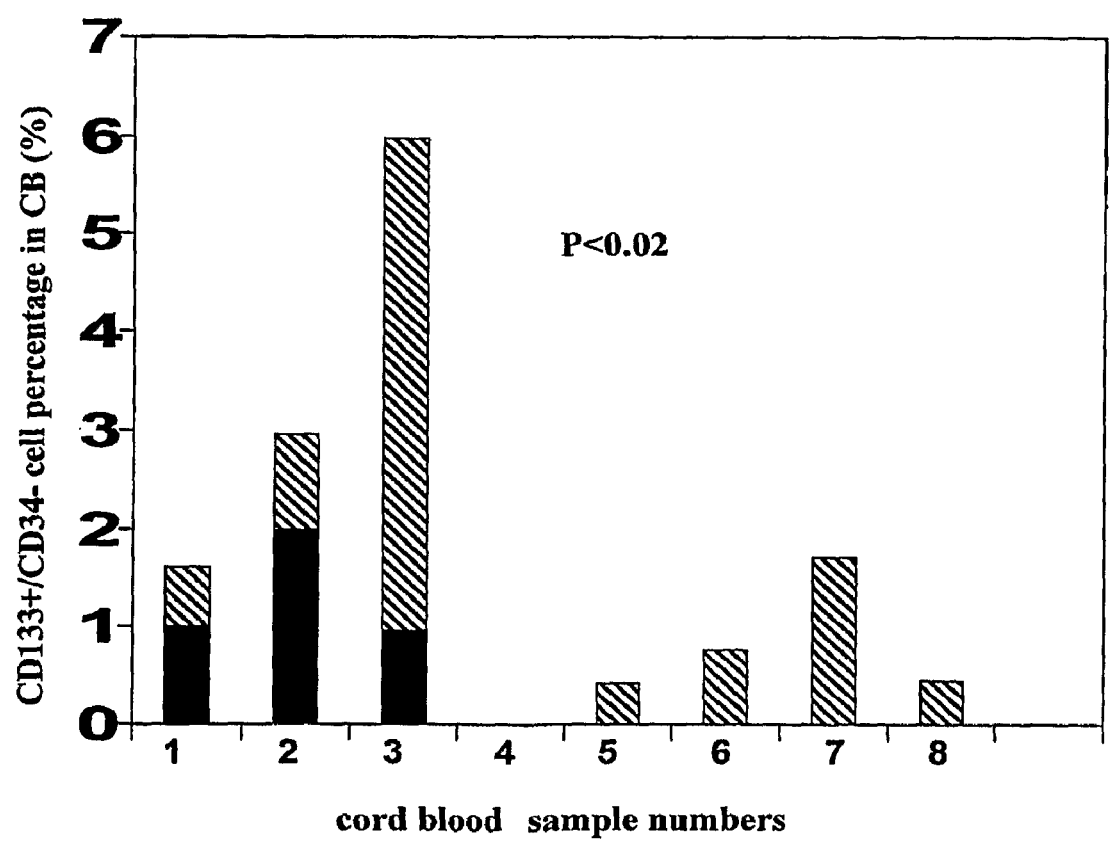
Figure 9B:
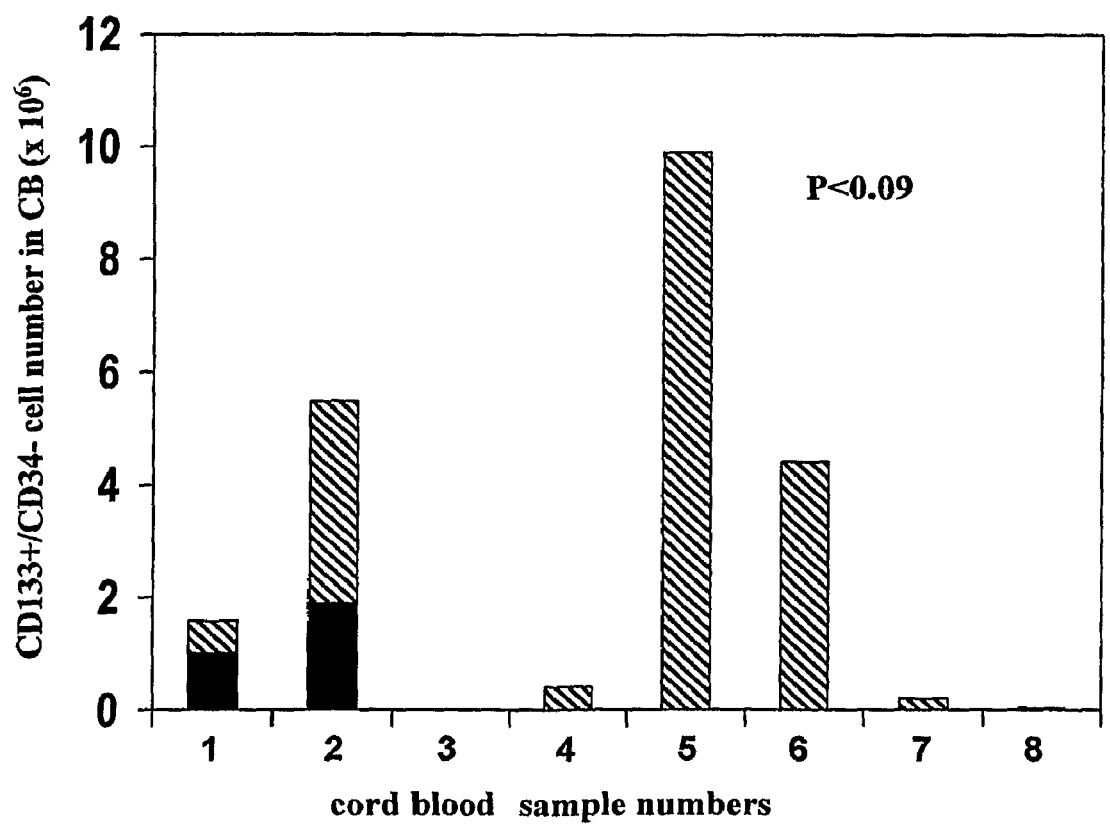

FIGS. 9A and 9B. The mean percentage and absolute number of CD133+/CD34− cells in venipuncture and pulsatile machine placenta perfusion fractions was 0.37±0.7% (mean±S.D.) (range 0-2), 0.36±0.7×10$^6$ (mean±S.D.) (range 0-1.9) and 1.16±1.5% (mean±S.D.) (range 0-5), 2.4±3.3×10$^6$ (mean±S.D.) (range 0-9.9), respectively, indicating that PMPP fraction contained 3 times enriched CD133+/CD34− and 6.6 times more CD133+/CD34− cell number.

Figure 10A:
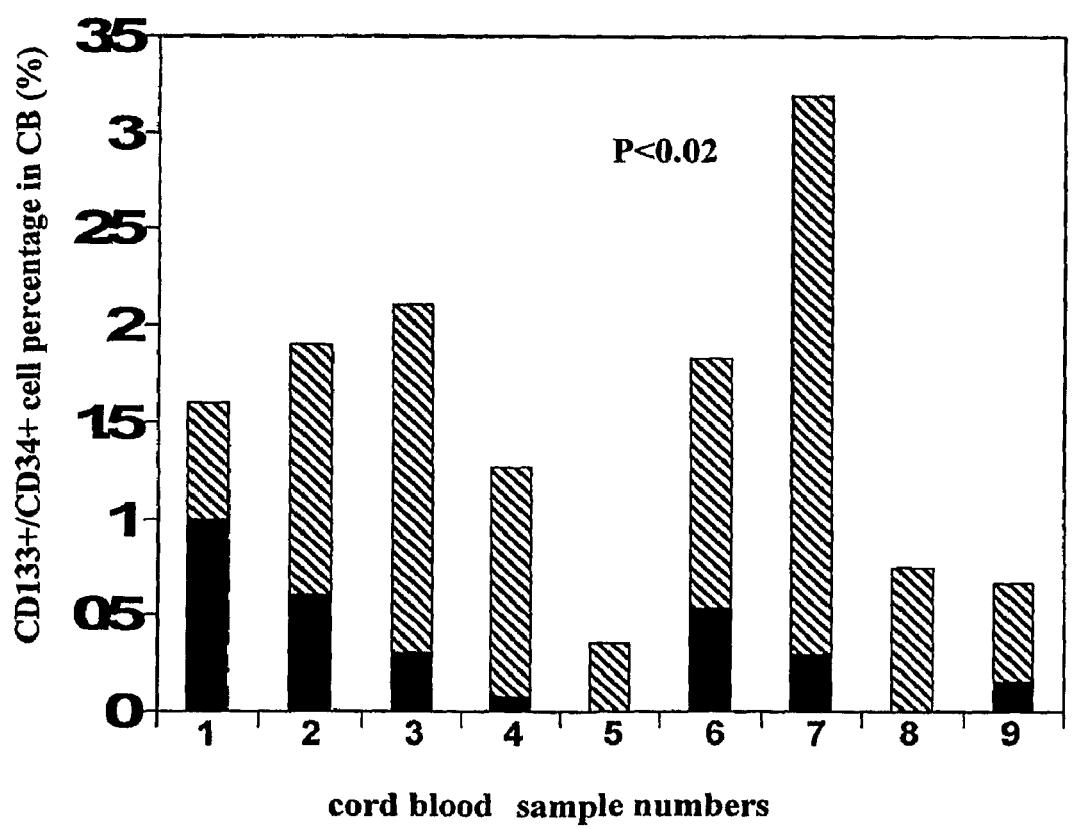
Figure 10B:
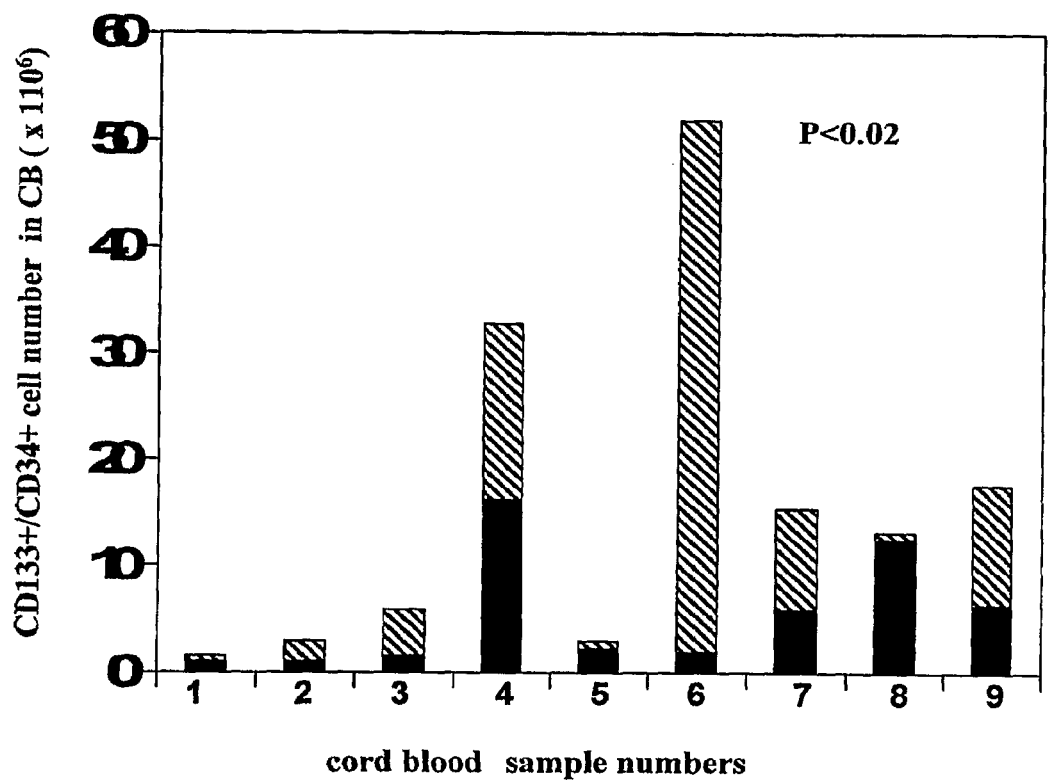

FIGS. 10A and 10B. The mean percentage and absolute number of CD133+/CD34+ cells in venipuncture and pulsatile machine placenta perfusion fractions was 0.62±0.5% (mean±S.D.) (range 0-0.6), 0.68±0.6×10$^6$ (mean±S.D.) (range 0-1.89) and 1.26±0.8% (mean±S.D.) (range 0.35-2.9), 4.0±5.6×10$^6$ (mean±S.D.) (range 0.35-16.5), respectively, demonstrating that PMPP contained 2 times enriched CD133+/CD34+ cells and 5.9-fold increase CD133+/CD34+ absolute cell number.

DETAILED DESCRIPTION OF THE INVENTION

In the following detailed description, the methods of the present invention can be performed in a number of different variations, and it is to be understood that other embodiments may be utilized and logical changes may be made without departing from the scope of the present invention. The following detailed description, therefore, is not to be taken in a limiting sense, and the scope of the present invention is defined by the appended claims.

Although a number of discrete embodiments are described below, it is to be understood that these are merely non-limiting examples, and that any given embodiment of the invention may comprise some of the features of one shown embodiment, and/or some of the features of another shown embodiment.

A method of collecting cord blood stem cells is described that can comprise or consist of perfusing, for example pulsatile perfusing, an isolated non-exsanguinated or partially exsanguinated mammalian (any species including horse) placenta with a perfusion solution to produce a perfusate comprising cord blood stem cells; collecting the perfusate comprising cord blood stem cells; and isolating cord blood stem cells from the perfusate to produce isolated cord blood stem cells.

In addition, a method is described wherein the perfusate, for example, resulting from pulsatile perfusion, plus aspiration of cord blood from the umbilical vasculature with a conventional exsanguination method results in at least a 1.5-fold increase in total mononuclear cell count obtained from one placenta compared to aspiration of cord blood from the umbilical vasculature with a needle and syringe alone.

A further method is described, wherein the perfusate, for example, resulting from pulsatile perfusion, plus aspiration of cord blood from the umbilical vasculature with a conventional exsanguination method results in at least a 2-fold increase, a>2-fold increase to a 10-fold increase, a 4-fold increase to a 6-fold increase, or a 5.5-fold increased percentage of CD34+ cells obtained compared to aspiration of cord blood from the umbilical vasculature with a needle and syringe alone.

A method is described, wherein the perfusate, for example, resulting from pulsatile perfusion, plus aspiration of cord blood from the umbilical vasculature with a conventional exsanguination method results in a 4.9-fold increased total CD34+ cells obtained compared to aspiration of cord blood from the umbilical vasculature with a needle and syringe alone.

Also, a method is described, wherein the perfusate, for example, resulting from pulsatile perfusion, plus aspiration of cord blood from the umbilical vasculature with a conventional exsanguination method results in at least a 5-fold increase, a>5-fold increase to a 20-fold increase, a 12-fold increase to an 18-fold increase, or a 14.8-fold increased CD34+/CD38− cell population percentage obtained compared to aspiration of cord blood from the umbilical vasculature with a needle and syringe alone.

A method is described, wherein the perfusate, for example, resulting from pulsatile perfusion, plus aspiration of cord blood from the umbilical vasculature with a conventional exsanguination method results in at least 5 times more, 5 times to 20 times more, 10 times to 15 times more, or 11 times more CD34+/CD38− cells being collected compared to aspiration of cord blood from the umbilical vasculature with a needle and syringe alone.

A further method is described, wherein the perfusate, for example, resulting from pulsatile perfusion, plus aspiration of cord blood from the umbilical vasculature with a conventional exsanguination method results in at least a 2-fold, a 2-fold to a 10-fold, a 4-fold to an 8-fold, or a 5-fold enriched CD133+ cell percentage obtained compared to aspiration of cord blood from the umbilical vasculature with a needle and syringe alone.

A method is described, wherein the perfusate, for example, resulting from pulsatile perfusion, plus aspiration of cord blood from the umbilical vasculature with a conventional exsanguination method results in at least a 3-fold, a 3-fold to a 15-fold, a 5-fold to an 19-fold, or a 7-fold higher CD133+ cell population obtained compared to aspiration of cord blood from the umbilical vasculature with a needle and syringe alone.

I. Definitions

The below definitions serve to provide a clear and consistent understanding of the specification and claims, including the scope to be given such terms.

Perfuse. The term "perfuse" or "perfusion" refers to the act of inducing a flow of a fluid over or through a non-exsanguinated or a partially exsanguinated placenta, preferably the passage of fluid through a non-exsanguinated or a partially exsanguinated placenta with sufficient force or pressure to remove any residual cells, e.g., non-attached cells from the organ or tissue. As used herein, the term "perfusate" refers to the fluid collected following its passage through an organ or tissue. In a preferred embodiment, the perfusate contains one or more anticoagulants. A flow of perfusion solution can comprise a pressure-mediated flow of perfusion solution. A pressure-mediated flow of solution can comprise a positive or negative pressure mediated flow of solution. A pressure mediated flow of solution can comprise a pulsatile flow of solution.

Perfusing can comprise perfusing with at least a first volume of perfusion solution for a period of time of from about 10 minutes to about 1 hour; from about 15 minutes to about 45 minutes; or from about 20 minutes to about 30 minutes.

Perfusing can comprise perfusing a non-exsanguinated or a partially exsanguinated placenta in an open or closed rigid or deformable container. The container can comprise a volume of perfusion solution such that the non-exsanguinated or a partially exsanguinated isolated placenta is submerged in the perfusion solution contained in the container during perfusing, whereby the volume of perfusion solution and the perfusion solution contained in the container are combined prior to isolating cord blood stem cells there from. The submerged isolated placenta and surrounding perfusion solution can be at ambient pressure or can be subjected to a positive and/or negative pressure.

Perfusing can comprise subjecting a non-exsanguinated or a partially exsanguinated placenta to a pulsatile flow of perfusion solution using a pulsatile or peristaltic pump, for example, at from about 15 to about 90 beats/min and at a systolic pressure of from about 15 to about 90 mmHg; or at about 60 beats/min and at a systolic pressure of from about 30 to about 70 mmHg.

The pressure source used to push or pull perfusion solution through the mammalian placenta will be sufficient to generate a flow of solution from a pressurized system, for example, a peristaltic or pulsatile pump or device. The use of peristaltic pumping systems facilitates retention of sterility in the solutions being induced to flow through the placenta. The actual pressure level or pumping rate is adjusted to optimize removal of cord blood from a partially exsanguinated or non-exsanguinated placenta.

Perfusion solution. The term "perfusion solution" means any physiologically compatible solution or media comprising an anticoagulant sufficient to sustain viability of cord blood cells comprising stem cells. Suitable perfusion solutions can comprise of consist of a RPMI (Roswell Park Memorial Institute) media, optionally comprising gluconate and/or heparin, for example 1000 U heparin for a total volume of 1 liter; and Belzer MPS optionally comprising heparin, for example 2000 U heparin for a total volume of 600-750 ml. Other suitable perfusion solutions are known and can be readily selected and employed by one of ordinary skill in the art. Perfusing can comprise perfusing with at least a first volume of perfusion solution. Perfusing can be carried out at a temperature of from about 4° C. to about 27° C., for example, at room temperature.

First Volume. The term "first volume" means a volume of a perfusion solution for perfusing a non-exsanguinated or partially exsanguinated isolated mammalian placenta. The first volume of perfusing solution can comprise or consist of from about 250 ml perfusion solution to about 2 liters, from about 400 ml to about 1.5 liters; from about 500 ml to about 1.2 liters, from about 600 ml to about 1 liter; and from about 600 ml to about 750 ml perfusion solution.

Pressure Mediated Flow. The term "pressure mediated flow" means a flow of perfusion solution induced by positive or negative pressure.

Negative Pressure. The term "negative pressure" means a pressure below atmospheric pressure, i.e., less than one atmosphere.

Positive Pressure. The term "positive pressure" means a pressure at or above one atmosphere, i.e., greater than or equal to one atmosphere.

Exsanguinated Placenta. The term "Exsanguinated Placenta" means an isolated placenta from which all circulating blood has been removed or withdrawn, i.e., to make bloodless.

Non-Exsanguinated. The term "Non-Exsanguinated Placenta" means an isolated placenta from which no circulating blood has been removed or withdrawn.

Partially-Exsanguinated. The term "Partially-Exsanguinated Placenta" means an isolated placenta from which a portion of the circulating blood has been removed or withdrawn.

Stem Cell. As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. The "stem cell" used herein includes "progenitor cells" unless otherwise noted.

Hematopoietic stem cells are rare primitive blood cell progenitors that have the capacity to self-replicate, so as to maintain a continuous source of regenerative cells, and to differentiate, so as to give rise to various morphologically recognizable precursors of blood cell lineages. These precursors are immature blood cells that cannot self-replicate and must differentiate into mature blood cells including the erythroid, lymphoid and myeloid cells. Within the bone marrow microenvironment, the stem cells self-proliferate and actively maintain continuous production of all mature blood cell lineages throughout life.

Human cord blood derived CD133+ cells carry characteristics of primitive hematopoietic cells that offer an alternative to CD34+ cells in hematopoietic stem cell transplantation (Jaatinen et al., 2006). Unlike CD34+ cells, CD133+ cells are considered to be highly noncommitted with the capacity to self-renew and differentiate. It is a more homogenous cell population than CD34+ cells. In addition, CD133+ cells have been shown to have a higher clonogenic capacity than CD34+/CD133− cells. CD133 expression is not necessarily associated with CD34 expression (Jaatinen et al., 2006).

CD34+ cells are defined as the earliest hematopoietic stem cell identifiable in bone marrow, peripheral blood or neonatal cord blood. The supplement and the medium of the present invention are particularly suited for supporting the expansion of CD34+ cells and cells of myeloid lineage, including BFU-E cells, erythrocytes, CFU-MEG cells, megakaryocytes, CFU-GM cells, monocytes, macrophages, neutrophils eosinophils, and basophils. In earlier stages of development, cells of myeloid lineage express the CD34+ marker protein. In later stages of development, cells of myeloid lineage do not express detectable levels of the CD34+ marker protein.

Whether a cord blood stem cell expresses the CD34+ marker protein can be determined by one of ordinary skill in the art using well-known techniques, such as fluorescence activated cell sorting.

"CD34+ hematopoietic cells" or "CD34+ cells" are hematopoietic cells which express the CD34+ surface marker protein. Such cells include but are not limited to hematopoietic stem cells, myeloid progenitor or precursor cells, erythroid progenitor or precursor cells, and lymphoid progenitor or precursor cells.

CD34+ cells can be isolated from collected cord blood and/or perfusate to produce isolated cord blood stem cells using methods that are well known by those of ordinary skill in the art. Various systems are available to those of ordinary skill in art. For example, the MicroCELLector System® (Applied Immune Sciences), the MiniMacs System (Miltenvi Biotec), the StemSep™ system (StemCell Technologies) can be used can be used to isolate CD34+ cells. To prepare a preparation of cells enriched for CD34+ cells on a larger scale, systems marketed by Baxter Healthcare and CellPro are available to those of ordinary skill in the art.

The terms "hematopoietic stem cell" and "pluripotent hematopoietic stem cell" refer to a cell which can give rise to any type of hematopoietic progenitor or precursor cell, including myeloid progenitor or precursor cells, erythroid progenitor or precursor cells, and lymphoid progenitor or precursor cells. Hematopoietic stem cells display a CD34+/CD133−/CD38− phenotype or a CD34+/HLD-DR.−/CD38− phenotype (Daley, J. P. et al., Focus 18:62-67 (1996); Pimentel, E., Ed., Handbook of Growth Factors Vol. III: Hematopoietic Growth Factors and Cytokines, pp. 1-2, CRC Press, Boca Raton, Fla., 1994).

1. Method of Collecting Placenta CB Cells with or without Prior Conventional CB Harvesting A proof of concept pilot test for a method for CB harvesting using a pulsatile perfusion technology using Waters' RM3 pulsative perfusion device (Waters Medical Systems, Rochester, Minn.) widely used for renal preservation was successful. The device was originally designed to improve the immediate function of the kidneys which are stored prior to transplant. The perfusion solution consisted of RPMI (Roswell Park Memorial Institute) media with gluconate and 1000 U heparin for a total of 1 liter or Belzer MPS plus 1000-2000 U heparin 600-750 ml Belzer MPS with 2000 U heparin sodium). Presently, it has been shown using a baboon placenta, the feasibility of this method and successful perfusion and removal of the entire remaining placenta CB. The collection of an absolute total mononuclear cell count, colony forming cell (CFC) count, CD34+ and CD34+/CD38− percentage and count was approximately 2-fold higher when machine perfusion was added to the conventional venipuncture method compared to venipuncture method alone.

Based on the promising baboon CB collection by pulsatile machine perfusion, this method was tested on human placentas. Eight CB collections were performed on 36-41 week placentas from 7 normal vaginal deliveries and one caesarian section under the clinical protocol approved by the University of Maryland Institutional Review Board. Partial CB collection was first done by venipuncture with needle/syringe to aspirate the maximal quantity possible as soon as the umbilical cord was clamped and the baby was delivered while the placenta was still in uterus. This method is used for both trans-vaginal and caesarian section to maximize the yield of CB collection and it is one of several methods used widely for routine CB collection. The 18 gauge needle was attached to 30 or 60 ml syringes and the aspirated CB material was immediately transferred to a 50 ml conical tube containing 5000 U of heparin solution. The collected CB was immediately mixed with heparin to prevent clotting and stored in an ice chest. The mean CB volume collected by this procedure was 59±18 ml (mean±S.D.) (range 40-90 ml). Next, the placenta was delivered routinely and placed directly into a sterile isolation bag (3M Health Care St. Paul, Minn.). If the placenta required visual examination, it was placed on a sterile tray and transferred into a sterile isolation bag at the time of completion of the examination. The placenta was weighed within the sterile bag as well. The sterile bag was tightly closed and placed into triple bag isolation and kept in an ice chest without any manipulations until the placenta perfusion was initiated. The placentas were perfused between 6.25 and 39 hours after delivery. A placenta can be cooled after isolation at a temperature of from about −3° C. to about 15° C., from about −8° C. to about 10° C., from about −2° C. to about 6° C., or from about 0° C. to about 6° C., provided the placenta is not permitted to freeze. The cooled placenta can be maintained prior to perfusing at a temperature above freezing, for example, at from about >0° C. to about 15° C., at about >0° C. to about 10° C., or at about 2° C. to about 6° C., for a period of time of from about 30 minutes to about 60 hours, from about 1 hour to about 50 hours; from about 6 hours to about 40 hours; from about 10 hours to about 40 hours; from about 15 hours to about 40 hours; or from about 20 hours to about 40 hours.

To perform pulsatile machine placental perfusion (PMPP), the placenta was placed on a sterile field and examined to determine whether there were any lacerations or tears in the placenta. Then, the umbilical cord was examined to look for 2 umbilical arteries and 1 umbilical cord vein. One or more of the two umbilical arteries and the umbilical vein were be canulated to facilitate perfusing. First, a 6 mm straight cannula was inserted into an umbilical cord vein and tied in place with o-silk tie, then; both arteries were each inserted with 2 mm straight cannulas and tied in place with o-silk ties. The placenta was placed onto a closed perfusion circuit (Waters RM3 kidney perfusion pump) which was primed with Belzer MPS plus 1000-2000 U heparin (600-750 ml Belzer MPS with 2000 U heparin sodium) at a temperature of 1° C. to 27° C. Belzer MPS is a FDA approved organ perfusate used for preservation of cadaver donated organs for transplantation (Gage et al., 1997). Pulsatile Machine perfusion was performed at 60 beats/min and the systolic pressure was at between 30-70 mmHg. The average time to complete perfusion was 26 minutes (range 20-30 min). To determine the completion of placental perfusion, we used the placenta tissue color change from a dusky blue color into a clear white color as a marker for a total evacuation of the vascular content in the placenta.

Eight CB samples were collected using venipuncture and machine placenta perfusion method from the same subject and their quantitative descriptions are summarized in Table I. The mean CB volume collected by venipuncture was as described above. The mean CB volume from the pulsatile machine placenta perfusion method was not measurable since the perfusate and CB was mixed at the end. The mean gestation of the harvested placenta was 38.6 weeks (range 36-41 weeks) and the mean placenta size for diameter and thickness was 20×1 cm (17–22×1 cm). The placentas were obtained from one caesarian section (sample 1) and 7 vaginal deliveries (sample 2-8). Mean time from placenta delivery to the initiation of perfusion was 17 hours (mean) (6.25-39 hours), and the duration time of placenta perfusion procedure was less than 30 min per placenta (mean 26 minutes, range 20-30 min) (Table I). There was thrombosis found in 3 placentas (samples 3, 5, and 6) and it was approximately 5%, 10%, and 7% of the total placenta area but not seen in other subjects. These placentas were packed in ice at a temperature of 4° C. in a thermally insulated chest between 19 and 39 hours until the initiation of perfusion. Overall, there was no difficulty in performing machine perfusion for every placenta we tested including those with thrombosis and no barotrauma was observed due to pulsatile machine perfusion.

TABLE I

Characteristics of cord blood collections from 8 placentas

| Sample no. | Gestation (week) | Placenta size (diameter × thickness cm) | Time to perfusion (hr) | Perfusion time (hr) | CB volume by syringe (ml) | Method of delivery | Blood clot in placenta (%) |
|---|---|---|---|---|---|---|---|
| 1 | 39 | 18 × 1 | 9.5 | 0.5 | 50 | caesarian | 0 |
| 2 | 39 | 19 × 1 | 7 | 0.5 | 80 | vaginal | 0 |
| 3 | 39 | 22 × 1 | 27 | 0.42 | 65 | vaginal | 5 |
| 4 | 40 | 21 × 1 | 15 | 0.37 | 62 | vaginal | 0 |
| 5 | 36 | 18 × 1 | 39 | 0.33 | 40 | vaginal | 10 |
| 6 | 40 | 25 × 1 | 19 | 0.42 | 90 | vaginal | 7 |
| 7 | 36 | 17 × 1 | 6.25 | 0.33 | 46 | vaginal | 0 |
| 8 | 40 | 21 × 1 | 12.5 | 0.6 | 40 | vaginal | 0 |

2. Analysis of Collected Solution from PMPP in Comparison to Conventional Cord Blood Harvesting Method.

CB Mononuclear Cell Isolation

CB cells obtained from venipuncture of the placental vasculature were first diluted with Iscove's modified Dulbecco's media (IMDM) at 1:5 and mononuclear cells were isolated by Ficoll-Hypaque (Sigma Diagnostic, St Louis, Mo.) density gradient centrifugation as described previously (Takebe et al., 2002). The layer containing mononuclear cells was gently aspirated, the cells washed twice with PBS solution and enumerated by cytometer. Cell viability was confirmed by trypan blue exclusion method. CB cells obtained via PMPP were processed similarly to the CB cells from venipuncture. However, these cells were mixed in a large volume of perfusate (650 to 800 ml total volume). This perfusate was aliquoted among several dozen or so 50 ml conical tubes which were centrifuged together at 1800 rpm for 20 minutes to obtain the buffy coat layer. Then, the cells were further separated for mononuclear cells with Ficoll-Hypaque density gradient centrifugation. CB cells were washed and enumerated as described above.

Flow Cytometry Analysis

Mononuclear cells were stained with monoclonal antibodies including anti-human CD38– FITC, CD34–APC (BD Pharmingen, San Jose, Calif.), AC133-PE (Miltenyi Biotech, Auburn, Calif.) and analyzed by Facstar-plus (Becton Dickinson) per manufacturer's instructions. Isotype controls were performed using appropriate antibodies in parallel for each sample.

CD34+Cell Selection

The aliquot of CB mononuclear cells obtained from Ficoll-Hypaque density gradient centrifugation were further isolated to enrich CD34+ cell population by magnetic cell separation method using the CD34 progenitor Cell Isolation Kit (Miltenyi Biotec) per manufacture's instructions. Purified cell number and viability was determined by cytometer and trypan blue exclusion test. Enrichment for CD34+ cells was confirmed by flow cytometry analysis, and each isolation batch showed greater than 90% CD34+ cell purity with viability above 95% by trypan blue exclusion method.

Methylcellulose Colony Forming Unit Assays.

Purified CB CD34+ cells ($3 \times 10^3$ per plate) were seeded into the 35-mm culture dishes as described previously (Takebe et al., 2002). Cells were cultured in the commercially available culture media, MethoCult (StemCell Technology, Vancouver, Canada), consisted of 1 ml IMDM, 1% methylcellulose, BSA, 2-mercaptoethanol, L-glutamine, insulin, transferrin, SCF, GM-CSF, IL-3, IL-6, G-CSF, and erythropoietin per manufacturer's instructions. At day 14, the colonies (larger than 50 cells) were enumerated from duplicated culture dishes.

TABLE II

Summary of colony forming units from 3 CB samples containing a matched pair sample from venipuncture method and machine placenta perfusion method.

| Sample number | CFU-GM (a) | | CFU-GEMM (b) | | BFU-E | |
|---|---|---|---|---|---|---|
| | *VP | **PL | VP | PL | VP | PL |
| 1 | 366 ± 59 | 110 ± 42 | 2 ± 0.7 | 6 ± 0.7 | 1 ± 0 | 0 |
| 2 | 608 ± 36 | 197 ± 36 | 4 ± 0.7 | 12 ± 1.4 | 0 | 7 ± 0.7 |
| 3 | 650 ± 173 | 243 ± 40 | 1 ± 1.4 | 9 ± 3 | 0 | 3 ± 1.4 |

CFU-GM: colony-forming unit-granulocyte macrophage
CFU-GEMM: colony-forming unit-granulocyte, erythrocyte, monocyte
BFU-E: burst forming unit-erythroid
a and b: paired t-test showed statistically significant ($p < 0.05$) differences between venipuncture and machine placenta perfusion.
*VP: venipuncture method
**PL: PMPP method

TABLE III

Phenotype characteristics of CB stem cells collected via venipuncture or PMPP method

| Patient No. | VP* TMNC*** | PL** TMNC | VP CD34+ | PL CD34+ | VP CD34+38– | PL CD34+/38– | VP CD34+38+ | PL CD34+38+ |
|---|---|---|---|---|---|---|---|---|
| Patient 1 | 50 × 10⁶ | 63 × 10⁶ | $1.1^a (2.2)^b$ | $2.7^a (44)^b$ | $0.12^a (0.2)^b$ | $0.92^a (1.5)^b$ | $1.0^a (2)^b$ | $1.9^a (3)^b$ |
| Patient 2 | 200 × 10⁶ | 72 × 10⁶ | 4.9 (2.5) | 6.3 (8) | 0.66 (0.3) | 1.98 (2.8) | 3.1 (1.5) | 4.3 (6) |
| Patient 3 | 770 × 10⁶ | 300 × 10⁶ | 15 (2) | 56.8 (18) | 2.7 (0.35) | 42 (14) | 16.2 (2) | 16.6 (5.5) |
| Patient 4 | 840 × 10⁶ | 100 × 10⁶ | 1.76 (0.2) | 2.25 (2.25) | 1.6 (0.19) | 1.43 (1.43) | 2.18 (.26) | 0.82 (0.82) |
| Patient 5 | 115 × 10⁶ | 1290 × 10⁶ | 2.4 (2) | 116 (9) | 0.44 (0.4) | 65 (5.1) | 1.9 (1.7) | 50 (3.9) |
| Patient 6 | 520 × 10⁶ | 260 × 10⁶ | 8.3 (1.6) | 28.6 (11) | 2.4 (0.46) | 19.2 (7.4) | 5.9 (1.14) | 9.5 (3.65) |

TABLE III-continued

Phenotype characteristics of CB stem cells collected via venipuncture or PMPP method

| Patient No. | VP* TMNC*** | PL** TMNC | VP CD34+ | PL CD34+ | VP CD34+38− | PL CD34+/38− | VP CD34+38+ | PL CD34+38+ |
|---|---|---|---|---|---|---|---|---|
| Patient 7 | 790 × 10$^6$ | 47 × 10$^6$ | 18.2 (2.23) | 1.6 (3.45) | 5.2 (0.66) | 0.86 (1.82) | 12.4 (1.57) | 0.78 (1.65) |
| Patient 8 | 1260 × 10$^6$ | 330 × 10$^6$ | 6.99 (0.55) | 16.1 (4.9) | 0.5 (0.04) | 4.29 (1.3) | 6.43 (0.51) | 11.2 (3.38) |

*VP: venipuncture method
**PL: PMPP method
***TMNC: total mononuclear cells
$^a$×10$^6$
$^b$percentage of total mononuclear cells

TABLE IV

Phenotype characteristics of CB stem cells collected via venipuncture or PMPP method

| Patient No. | VP* CD133+ | PL** CD133+ | VP CD133+34+ | PL CD133+34+ | VP CD133+38− | PL CD133+38− | VP CD133+34− | PL CD133+34− |
|---|---|---|---|---|---|---|---|---|
| Patient 1 | 1.3$^a$ (1.0)$^b$ | 1.4$^a$ (2.3)$^b$ | 0.32$^a$ (0.6)$^b$ | 0.84$^a$ (13)$^b$ | 0.08$^a$ (.15)$^b$ | 0.61$^a$ (.97)$^b$ | 1$^a$ (2)$^b$ | 0.6$^a$ (0.96)$^b$ |
| Patient 2 | 2.3 (2.5) | 4.9 (6.8) | 0.6 (0.3) | 1.3 (1.8) | 1.1 (0.57) | 4.1 (5.6) | 1.9 (0.97) | 3.6 (5) |
| Patient 3 | 0.46 (.06) | 3.8 (1.2) | 0.54 (.07) | 3.7 (1.2) | 0 (0) | 3.7 (1.25) | 0 (0) | 0 (0) |
| Patient 4 | 0 (0) | 0.8 (0.8) | 0 (0) | 0.35 (0.35) | 0 (0) | 0.88 (.88) | 0 (0) | 0.43 (.43) |
| Patient 5 | 0.43 (.37) | 26 (2.1) | 0.6 (0.53) | 16.5 (1.3) | 0 (0) | 27 (2.1) | 0 (0) | 9.9 (0.77) |
| Patient 6 | 1.8 (0.35) | 11.2 (4.3) | 1.5 (0.29) | 7.5 (2.9) | 0.4 (0.08) | 9.5 (3.65) | 0 (0) | 4.4 (1.7) |
| Patient 7 | 0 (0) | 0.55 (1.18) | 0 (0) | 0.35 (0.74) | 0 (0) | 0.49 (1.04) | 0 (0) | 0.21 (0.44) |
| Patient 8 | 1.51 (0.12) | 1.65 (0.5) | 1.89 (0.15) | 1.68 (0.51) | 0 (0) | 2.54 (0.77) | 0 (0) | 0.03 (0.01) |

*VP: venipuncture method
**PL: PMPP method
**TMNC: total mononuclear cells
$^a$×10$^6$
$^b$percentage of total mononuclear cells

REFERENCES

ALMEIDA-PORADA, G., PORADA, C. D., CHAMBERLAIN, J., TORABI, A., and ZANJANI, E. D. (2004). Formation of human hepatocytes by human hematopoietic stem cells in sheep. Blood 104, 2582-2590.

AZIZI, S. A., STOKES, D., AUGELLI, B. J., DIGIROLAMO, C., and PROCKOP, D. J. (1998). Engraftment and migration of human bone marrow stromal cells implanted in the brains of albino rats—similarities to astrocyte grafts. Proc Natl Acad Sci USA 95, 3908-3913.

BARKER, J. N., KREPSKI, T. P., DEFOR, T. E., DAVIES, S. M., WAGNER, J. E., and WEISDORF, D. J. (2002). Searching for unrelated donor hematopoietic stem cells: availability and use of umbilical cord blood versus bone marrow. Biol Blood Marrow Transplant 8, 257-260.

BELVEDERE, O., FERUGLIO, C., MALANGONE, W., BONORA, M. L., MINISINI, A. M., SPIZZO, R., DONINI, A., SALA, P., DE ANNA, D., HILBERT, D. M., and DEGRASSI, A. (2000). Increased blood volume and CD34(+) CD38(−) progenitor cell recovery using a novel umbilical cord blood collection system. Stem Cells 18, 245-251.

BERTOLINI, F., LAZZARI, L., LAURI, E., CORSINI, C., CASTELLI, C., GORINI, F., and SIRCHIA, G. (1995). Comparative study of different procedures for the collection and banking of umbilical cord blood. J Hematother 4, 29-36.

BHATTACHARYA, S., JACKSON, J. D., DAS, A. V., THORESON, W. B., KUSZYNSKI, C., JAMES, J., JOSHI, S., and AHMAD, I. (2003). Direct identification and enrichment of retinal stem cells/progenitors by Hoechst dye efflux assay. Invest Opthalmol Vis Sci 44, 2764-2773.

BICKNESE, A. R., GOODWIN, H. S., QUINN, C. O., HENDERSON, V. C., CHIEN, S. N., and WALL, D. A. (2002). Human umbilical cord blood cells can be induced to express markers for neurons and glia. Cell Transplant 11, 261-264.

BRAZELTON, T. R., ROSSI, F. M., KESHET, G. I., and BLAU, H. M. (2000). From marrow to brain: expression of neuronal phenotypes in adult mice. Science 290, 1775-1779.

CAI, J., CHENG, A., LUO, Y., LU, C., MATTSON, M. P., RAO, M. S., and FURUKAWA, K. (2004a). Membrane properties of rat embryonic multipotent neural stem cells. J Neurochem 88, 212-226.

CAI, J., WEISS, M. L., and RAO, M. S. (2004b). In search of "stemness". Exp Hematol 32, 585-598.

CAI, J., WU, Y., MIRUA, T., PIERCE, J. L., LUCERO, M. T., ALBERTINE, K. H., SPANGRUDE, G. J., and RAO, M. S. (2002). Properties of a fetal multipotent neural stem cell (NEP cell). Dev Biol 251, 221-240.

CAMARGO, F. D., FINEGOLD, M., and GOODELL, M. A. (2004). Hematopoietic myelomonocytic cells are the major source of hepatocyte fusion partners. J Clin Invest 113, 1266-1270.

CHEN, N., HUDSON, J. E., WALCZAK, P., MISIUTA, I., GARBUZOVA-DAVIS, S., JIANG, L., SANCHEZ-RAMOS, J., SANBERG, P. R., ZIGOVA, T., and WILLING, A. E. (2005). Human Umbilical Cord Blood Progenitors: The Potential of These Hematopoietic Cells to Become Neural. Stem cells (Dayton, Ohio).

COGLE, C. R., YACHNIS, A. T., LAYWELL, E. D., ZANDER, D. S., WINGARD, J. R., STEINDLER, D. A., and SCOTT, E. W. (2004). Bone marrow transdifferentiation in brain after transplantation: a retrospective study. Lancet 363, 1432-1437.

CORTI, S., LOCATELLI, F., PAPADIMITRIOU, D., DONADONI, C., DEL BO, R., CRIMI, M., BORDONI, A., FORTUNATO, F., STRAZZER, S., MENOZZI, G., SALANI, S., BRESOLIN, N., and COMI, G. P. (2006). Transplanted ALDHhiSSClo neural stem cells generate motor neurons and delay disease progression of nmd mice, an animal model of SMARD1. Hum Mol Genet 15, 167-187.

DONALDSON, C., ARMITAGE, W. J., LAUNDY, V., BARRON, C., BUCHANAN, R., WEBSTER, J., BRADLEY, B., and HOWS, J. (1999). Impact of obstetric factors on cord blood donation for transplantation. British journal of haematology 106, 128-132.

EGLITIS, M. A., and MEZEY, E. (1997). Hematopoietic cells differentiate into both microglia and macroglia in the brains of adult mice. Proc Natl Acad Sci USA 94, 4080-4085.

ESCOLAR, M. L., POE, M. D., PROVENZALE, J. M., RICHARDS, K. C., ALLISON, J., WOOD, S., WENGER, D. A., PIETRYGA, D., WALL, D., CHAMPAGNE, M., MORSE, R., KRIVIT, W., and KURTZBERG, J. (2005). Transplantation of umbilical-cord blood in babies with infantile Krabbe's disease. N Engl J Med 352, 2069-2081.

FERRARI, G., CUSELLA-DE ANGELIS, G., COLETTA, M., PAOLUCCI, E., STORNAIUOLO, A., COSSU, G., and MAVILIO, F. (1998). Muscle regeneration by bone marrow-derived myogenic progenitors. Science 279, 1528-1530.

FORRAZ, N., PETTENGELL, R., and MCGUCKIN, C. P. (2004). Characterization of a lineage-negative stem-progenitor cell population optimized for ex vivo expansion and enriched for LTC-IC. Stem cells (Dayton, Ohio) 22, 100-108.

FORTUNEL, N. O., OTU, H. H., NG, H. H., CHEN, J., MU, X., CHEVASSUT, T., LI, X., JOSEPH, M., BAILEY, C., HATZFELD, J. A., HATZFELD, A., USTA, F., VEGA, V. B., LONG, P. M., LIBERMANN, T. A., and LIM, B. (2003). Comment on "'Stemness': transcriptional profiling of embryonic and adult stem cells" and "a stem cell molecular signature". Science 302, 393; author reply 393.

GAGE, F., BARHYTE, D. Y., KOWALSKI, A. E., LIGHT, J. A., WILMER, R., and CALLENDER, C. O. (1997). A comparison study of the Belzer machine preservation solution with and without penicillin. Transplant Proc 29, 3643.

GEKAS, C., DIETERLEN-LIEVRE, F., ORKIN, S. H., and MIKKOLA, H. K. (2005). The placenta is a niche for hematopoietic stem cells. Dev Cell 8, 365-375.

GEORGE, T. J., SUGRUE, M. W., GEORGE, S. N., and WINGARD, J. R. (2006). Factors associated with parameters of engraftment potential of umbilical cord blood. Transfusion 46, 1803-1812.

GLUCKMAN, E., ROCHA, V., BOYER-CHAMMARD, A., LOCATELLI, F., ARCESE, W., PASQUINI, R., ORTEGA, J., SOUILLET, G., FERREIRA, E., LAPORTE, J. P., FERNANDEZ, M., and CHASTANG, C. (1997). Outcome of cord-blood transplantation from related and unrelated donors. Eurocord Transplant Group and the European Blood and Marrow Transplantation Group. N Engl J Med 337, 373-381.

GOODWIN, H. S., BICKNESE, A. R., CHIEN, S. N., BOGUCKI, B. D., QUINN, C. O., and WALL, D. A. (2001). Multilineage differentiation activity by cells isolated from umbilical cord blood: expression of bone, fat, and neural markers. Biol Blood Marrow Transplant 7, 581-588.

HARRIS, D. T., SCHUMACHER, M. J., RYCHLIK, S., BOOTH, A., ACEVEDO, A., RUBINSTEIN, P., BARD, J., and BOYSE, E. A. (1994). Collection, separation and cryopreservation of umbilical cord blood for use in transplantation. Bone marrow transplantation 13, 135-143.

HRUBAN, R. H., LONG, P. P., PERLMAN, E. J., HUTCHINS, G. M., BAUMGARTNER, W. A., BAUGHMAN, K. L., and GRIFFIN, C. A. (1993). Fluorescence in situ hybridization for the Y-chromosome can be used to detect cells of recipient origin in allografted hearts following cardiac transplantation. Am J Pathol 142, 975-980.

JAATINEN, T., HEMMORANTA, H., HAUTANIEMI, S., NIEMI, J., NICORICI, D., LAINE, J., YLI-HARJA, O., AND PARTANEN, J. (2006). Global Gene Expression Profile of Human Cord Blood-Derived CD133+Cells. Stem Cells 24, 631-641.

KIM, M., TURNQUIST, H., JACKSON, J., SGAGIAS, M., YAN, Y., GONG, M., DEAN, M., SHARP, J. G., and COWAN, K. (2002). The multidrug resistance transporter ABCG2 (breast cancer resistance protein 1) effluxes Hoechst 33342 and is overexpressed in hematopoietic stem cells. Clin Cancer Res 8, 22-28.

KORBLING, M., KATZ, R. L., KHANNA, A., RUIFROK, A. C., RONDON, G., ALBITAR, M., CHAMPLIN, R. E., and ESTROV, Z. (2002). Hepatocytes and epithelial cells of donor origin in recipients of peripheral-blood stem cells. N Engl J Med 346, 738-746.

KUCI, S., WESSELS, J. T., BUHRING, H. J., SCHILBACH, K., SCHUMM, M., SEITZ, G., LOFFLER, J., BADER, P., SCHLEGEL, P. G., NIETHAMMER, D., and HANDGRETINGER, R. (2003). Identification of a novel class of human adherent CD34– stem cells that give rise to SCID-repopulating cells. Blood 101, 869-876.

KUCIA, M., HALASA, M., WYSOCZYNSKI, M., BASKIEWICZ-MASIUK, M., MOLDENHAWER, S., ZUBA-SURMA, E., CZAJKA, R., WOJAKOWSKI, W., MACHALINSKI, B., and RATAJCZAK, M. Z. (2006). Morphological and molecular characterization of novel population of CXCR4(+) SSEA-4(+) Oct-4(+) very small embryonic-like cells purified from human cord blood-preliminary report. Leukemia.

KURTZBERG, J., LAUGHLIN, M., GRAHAM, M. L., SMITH, C., OLSON, J. F., HALPERIN, E. C., CIOCCI, G., CARRIER, C., STEVENS, C. E., and RUBINSTEIN, P. (1996). Placental blood as a source of hematopoietic stem cells for transplantation into unrelated recipients. N Engl J Med 335, 157-166.

LAGASSE, E., CONNORS, H., AL-DHALIMY, M., REITSMA, M., DOHSE, M., OSBORNE, L., WANG, X., FINEGOLD, M., WEISSMAN, I. L., and GROMPE, M. (2000). Purified hematopoietic stem cells can differentiate into hepatocytes in vivo. Nat Med 6, 1229-1234.

LASKY, L. C., LANE, T. A., MILLER, J. P., LINDGREN, B., PATTERSON, H. A., HALEY, N. R., and BALLEN, K. (2002). In utero or ex utero cord blood collection: which is better? Transfusion 42, 1261-1267.

LAUGHLIN, M. J., EAPEN, M., RUBINSTEIN, P., WAGNER, J. E., ZHANG, M. J., CHAMPLIN, R. E., STEVENS, C., BARKER, J. N., GALE, R. P., LAZARUS, H. M., MARKS, D. I., VAN ROOD, J. J., SCARADAVOU, A., and HOROWITZ, M. M. (2004). Outcomes after transplantation of cord blood or bone marrow from unrelated donors in adults with leukemia. N Engl J Med 351, 2265-2275.

LEESER, D. B., BINGAMAN, A. W., POLIAKOVA, L., SHI, Q., GAGE, F., BARTLETT, S. T., and FARNEY, A. C. (2004). Pulsatile pump perfusion of pancreata before human islet cell isolation. Transplant Proc 36, 1050-1051.

MCGUCKIN, C. P., FORRAZ, N., ALLOUARD, Q., and PETTENGELL, R. (2004). Umbilical cord blood stem cells can expand hematopoietic and neuroglial progenitors in vitro. Exp Cell Res 295, 350-359.

MCGUCKIN, C. P., FORRAZ, N., BARADEZ, M. O., NAVRAN, S., ZHAO, J., URBAN, R., TILTON, R., and DENNER, L. (2005). Production of stem cells with embryonic characteristics from human umbilical cord blood. Cell Prolif 38, 245-255.

MEZEY, E., CHANDROSS, K. J., HARTA, G., MAKI, R. A., and MCKERCHER, S. R. (2000). Turning blood into brain: cells bearing neuronal antigens generated in vivo from bone marrow. Science 290, 1779-1782.

MIGISHIMA, F., OIKAWA, A., KONDO, S., EMA, H., MORITA, Y., NAKAUCHI, H., YOKOYAMA, M., SONG, S. Y., NISHIJIMA, M., OKABE, M., and SHINOHARA, N. (2003). Full reconstitution of hematopoietic system by murine umbilical cord blood. Transplantation 75, 1820-1826.

MULLER, P., PFEIFFER, P., KOGLIN, J., SCHAFERS, H. J., SEELAND, U., JANZEN, I., URBSCHAT, S., and BOHM, M. (2002). Cardiomyocytes of noncardiac origin in myocardial biopsies of human transplanted hearts. Circulation 106, 31-35.

OKAMOTO, R., YAJIMA, T., YAMAZAKI, M., KANAI, T., MUKAI, M., OKAMOTO, S., IKEDA, Y., HIBI, T., INAZAWA, J., and WATANABE, M. (2002). Damaged epithelia regenerated by bone marrow-derived cells in the human gastrointestinal tract. Nat Med 8, 1011-1017.

OTTERSBACH, K., and DZIERZAK, E. (2005). The murine placenta contains hematopoietic stem cells within the vascular labyrinth region. Dev Cell 8, 377-387.

PARMAR, K., SAUK-SCHUBERT, C., BURDICK, D., HANDLEY, M., and MAUCH, P. (2003). Sca+CD34− murine side population cells are highly enriched for primitive stem cells. Exp Hematol 31, 244-250.

PAROLINI, O., ALVIANO, F., et al. (2008). Concise Review: Isolation and Characterization of Cells from Human Term Placenta: Outcome of the First International Workshop on Placenta Derived Stem Cells. Stem Cells 26, 300-311.

PETERSEN, B. E., BOWEN, W. C., PATRENE, K. D., MARS, W. M., SULLIVAN, A. K., MURASE, N., BOGGS, S. S., GREENBERGER, J. S., and GOFF, J. P. (1999). Bone marrow as a potential source of hepatic oval cells. Science 284, 1168-1170.

QUAINI, F., URBANEK, K., BELTRAMI, A. P., FINATO, N., BELTRAMI, C. A., NADAL-GINARD, B., KAJSTURA, J., LERI, A., and ANVERSA, P. (2002). Chimerism of the transplanted heart. N Engl J Med 346, 5-15.

RUBINSTEIN, P., CARRIER, C., SCARADAVOU, A., KURTZBERG, J., ADAMSON, J., MIGLIACCIO, A. R., BERKOWITZ, R. L., CABBAD, M., DOBRILA, N. L., TAYLOR, P. E., ROSENFIELD, R. E., and STEVENS, C. E. (1998). Outcomes among 562 recipients of placental-blood transplants from unrelated donors. N Engl J Med 339, 1565-1577.

RUBINSTEIN, P., ROSENFIELD, R. E., ADAMSON, J. W., and STEVENS, C. E. (1993). Stored placental blood for unrelated bone marrow reconstitution. Blood 81, 1679-1690.

SANCHEZ-RAMOS, J., SONG, S., CARDOZO-PELAEZ, F., HAZZI, C., STEDEFORD, T., WILLING, A., FREEMAN, T. B., SAPORTA, S., JANSSEN, W., PATEL, N., COOPER, D. R., and SANBERG, P. R. (2000). Adult bone marrow stromal cells differentiate into neural cells in vitro. Exp Neurol 164, 247-256.

SANCHEZ-RAMOS, J. R. (2002). Neural cells derived from adult bone marrow and umbilical cord blood. J Neurosci Res 69, 880-893.

SANCHEZ-RAMOS, J. R., SONG, S., KAMATH, S. G., ZIGOVA, T., WILLING, A., CARDOZO-PELAEZ, F., STEDEFORD, T., CHOPP, M., and SANBERG, P. R. (2001). Expression of neural markers in human umbilical cord blood. Exp Neurol 171, 109-115.

SCHARENBERG, C. W., HARKEY, M. A., and TOROK-STORB, B. (2002). The ABCG2 transporter is an efficient Hoechst 33342 efflux pump and is preferentially expressed by immature human hematopoietic progenitors. Blood 99, 507-512.

SHLEBAK, A. A., ROBERTS, I. A., STEVENS, T. A., SYZDLO, R. M., GOLDMAN, J. M., and GORDON, M. Y. (1998). The impact of antenatal and perinatal variables on cord blood haemopoietic stem/progenitor cell yield available for transplantation. Br J Haematol 103, 1167-1171.

STORMS, R. W., TRUJILLO, A. P., SPRINGER, J. B., SHAH, L., COLVIN, O. M., LUDEMAN, S. M., and SMITH, C. (1999). Isolation of primitive human hematopoietic progenitors on the basis of aldehyde dehydrogenase activity. Proc Natl Acad Sci USA 96, 9118-9123.

TAKEBE, N., XU, L. C., MACKENZIE, K. L., BERTINO, J. R., and MOORE, M. A. (2002). Methotrexate selection of long-term culture initiating cells following transduction of CD34(+) cells with a retrovirus containing a mutated human dihydrofolate reductase gene. Cancer Gene Ther 9, 308-320.

TAKEBE, N., ZHAO, S. C., ADHIKARI, D., MINEISHI, S., SADELAIN, M., HILTON, J., COLVIN, M., BANERJEE, D., and BERTINO, J. R. (2001). Generation of dual resistance to 4-hydroperoxycyclophosphamide and methotrexate by retroviral transfer of the human aldehyde dehydrogenase class 1 gene and a mutated dihydrofolate reductase gene. Mol Ther 3, 88-96.

THEISE, N. D., NIMMAKAYALU, M., GARDNER, R., ILLEI, P. B., MORGAN, G., TEPERMAN, L., HENEGARIU, O., and KRAUSE, D. S. (2000). Liver from bone marrow in humans. Hepatology 32, 11-16.

TURNER, C. W., LUZINS, J., and HUTCHESON, C. (1992). A modified harvest technique for cord blood hematopoietic stem cells. Bone marrow transplantation 10, 89-91.

WAGNER, J. E., BARKER, J. N., DEFOR, T. E., BAKER, K. S., BLAZAR, B. R., EIDE, C., GOLDMAN, A., KERSEY, J., KRIVIT, W., MACMILLAN, M. L., ORCHARD, P. J., PETERS, C., WEISDORF, D. J., RAMSAY, N. K., and DAVIES, S. M. (2002). Transplantation of unrelated donor umbilical cord blood in 102 patients with malignant and nonmalignant diseases: influence of CD34 cell dose and HLA disparity on treatment-related mortality and survival. Blood 100, 1611-1618.

WAGNER, J. E., BROXMEYER, H. E., and COOPER, S. (1992). Umbilical cord and placental blood hematopoietic stem cells: collection, cryopreservation, and storage. J Hematother 1, 167-173.

WAGNER, J. E., ROSENTHAL, J., SWEETMAN, R., SHU, X. O., DAVIES, S. M., RAMSAY, N. K., MCGLAVE, P. B., SENDER, L., and CAIRO, M. S. (1996). Successful transplantation of HLA-matched and HLA-mismatched umbilical cord blood from unrelated donors: analysis of engraftment and acute graft-versus-host disease. Blood 88, 795-802.

WANG, X., GE, S., MCNAMARA, G., HAO, Q. L., CROOKS, G. M., and NOLTA, J. A. (2003a). Albumin-expressing hepatocyte-like cells develop in the livers of immune-deficient mice that received transplants of highly purified human hematopoietic stem cells. Blood 101, 4201-4208.

WANG, X., WILLENBRING, H., AKKARI, Y., TORIMARU, Y., FOSTER, M., AL-DHALIMY, M., LAGASSE, E., FINEGOLD, M., OLSON, S., and GROMPE, M. (2003b). Cell fusion is the principal source of bone-marrow-derived hepatocytes. Nature 422, 897-901.

ZHOU, S., SCHUETZ, J. D., BUNTING, K. D., COLAPIETRO, A. M., SAMPATH, J., MORRIS, J. J., LAGUTINA, I., GROSVELD, G. C., OSAWA, M., NAKAUCHI, H., and SORRENTINO, B. P. (2001). The ABC transporter Bcrp1/ABCG2 is expressed in a wide variety of stem cells and is a molecular determinant of the side-population phenotype. Nat Med 7, 1028-1034.

ZIGOVA, T., SONG, S., WILLING, A. E., HUDSON, J. E., NEWMAN, M. B., SAPORTA, S., SANCHEZ-RAMOS, J., and SANBERG, P. R. (2002). Human umbilical cord blood cells express neural antigens after transplantation into the developing rat brain. Cell Transplant 11, 265-274.

Having described the invention in detail and by reference to the embodiments thereof, it will be apparent that modifications and variations are possible, including the addition of elements or the rearrangement or combination or one or more elements, without departing from the scope of the invention which is defined in the appended claims. Thus, the present invention is not intended to be limited to the embodiments shown herein but is to be accorded the widest scope consistent with the principles and novel features disclosed herein.

What is claimed is:

1. A method of isolating cord blood stem cells, comprising:
providing an isolated mammalian placenta comprising cord blood comprising cord blood stem cells, wherein said isolated mammalian placenta is non-exsanguinated;
performing machine perfusion of the isolated mammalian placenta with a pressure mediated pulsatile flow of a perfusion solution to produce a perfusate comprising cord blood comprising cord blood stem cells;
collecting the perfusate; and
isolating the cord blood stem cells from the perfusate to produce isolated cord blood stem cells.

2. A method of isolating cord blood stem cells, comprising:
providing an isolated mammalian placenta comprising cord blood comprising cord blood stem cells, wherein said isolated mammalian placenta is partially exsanguinated to produce a volume of cord blood comprising a first population of isolated cord blood stem cells;
conducting machine perfusion of the isolated mammalian placenta with pressure mediated perfusion solution to produce a perfusate comprising cord blood comprising cord blood stem cells, wherein said machine perfusion is performed using a pump;
collecting the perfusate; and
isolating the cord blood stem cell from the perfusate to produce a second population of isolated cord blood stem cells,
wherein said second population of isolated cord blood cells has a greater percentage of CD133+ cells than said first population of isolated cord blood cells.

3. The method according to claim 2, wherein said isolated mammalian placenta has been partially exsanguinated by venipuncture.

4. The method according to claim 2, wherein said isolated mammalian placenta has been partially exsanguinated by gravity drainage.

5. The method according to claim 1, wherein performing machine perfusion is carried out under conditions sufficient to produce a mammalian placenta substantially free from cord blood stem cells.

6. The method according to claim 1, further comprising:
cooling the isolated mammalian placenta to produce a cooled mammalian placenta;
said cooling the isolated mammalian placenta being performed prior to said performing machine perfusion.

7. The method accord to claim 6, further comprising:
maintaining the cooled isolated mammalian placenta at a temperature of about >0° to about 15° C. prior to said performing machine perfusion.

8. The method according to claim 6, further comprising:
maintaining the cooled isolated mammalian placenta at a temperature of from about >0° C. to about 6° C.

9. The method according to claim 6, further comprising:
maintaining the cooled isolated mammalian placenta at a temperature of from about >0° C. to about 15° C. for a period of time of up to about 40 hours.

10. The method according to claim 6, further comprising:
maintaining the cooled isolated mammalian placenta at a temperature of from about >0° C. to about 15° C. for a period of time of from 6 to 40 hours.

11. The method according to claim 6, further comprising:
maintaining the cooled isolated mammalian placenta at a temperature of from about >0° C. to about 15° C. for a period of time of from 10 to 40 hours.

12. The method according to claim 6, further comprising:
maintaining the cooled isolated mammalian placenta at a temperature of from about >0° C. to about 15° C. for a period of time of from 20 to 40 hours.

13. The method according to claim 6, wherein said cooling comprises placing said isolated mammalian placenta in ice.

14. The method according to claim 1, wherein the placenta is not administered or injected with an anticoagulant prior to said performing machine perfusion.

15. The method according to claim 1, wherein the perfusion solution comprises a physiologically-compatible solution comprising an anticoagulant.

16. The method according to claim 1, wherein the perfusion solution comprises one or more anticoagulants selected from the group consisting of heparin, creatine phosphate dextrose (CPDA), or a combination thereof.

17. The method according to claim 1, wherein said machine perfusion comprises perfusing via one or more of the umbilical arteries and the umbilical vein.

18. The method according to claim 17, wherein said perfusing further comprises cannulating one or more of the umbilical arteries and the umbilical vein to produce a cannulated placenta; and placing the cannulated placenta in a closed perfusion circuit.

19. The method according to claim 18, wherein said perfusing is carried out at a pulse setting of from about 15 beats/min to about 60 beats/min.

20. The method according to claim 18, wherein said perfusing is carried out at a pulse setting of about 60 beats/min.

21. The method according to claim 19, wherein said perfusing is carried out at a systolic pressure of from about 30 min Hg to about 70 mm Hg.

22. The method according to claim 21, wherein said perfusing is carried out for a period of time of from about 15 min. to about 35 min.

23. The method according to claim 1, wherein:
said isolated cord blood stem cells from the perfusate comprise a percentage of CD133+ cells which exceeds a percentage of CD133+ cells from a control sample, wherein said control sample comprises isolated cord blood stem cells isolated by partially exsanguinating a control non-exsanguinated mammalian placenta without performing machine perfusion on said control non-exsanguinated mammalian placenta.

24. The method according to claim 23, wherein the isolated cord blood stem cells from the perfusate further comprise cells selected from the group consisting of CD34+/CD38− cells, CD133+/CD34+ cells, CD133+/CD34− cells, CD117+ cells, CD90+ cells, CD59+ cells, Thy1+ cells, Lin− cells, CXCR4+ cells, ALDH$^{high}$ cells, side population (SP) cells, SSEA-3+ cells, SSEA-4+ cells, TRA-1-60 cells, TRA-1-81 cells, and combinations thereof.

25. The method according to claim 23, wherein the isolated cord blood stem cells from the perfusate further comprise stem cells that can differentiate into cells other than CD34+/CD38− cells, CD133+ cells, CD133+/CD34+ cells, CD133+/CD34− cells, CD117+ cells, CD90+ cells, CD59+ cells, Thy1+ cells, Lin− cells, CXCR4+ cells, ALDH$^{high}$ cells, side population (SP) cells, SSEA-3+ cells, SSEA-4+ cells, TRA-1-60 cells, or TRA-1-81 cells.

26. The method according to claim 23, wherein said isolated cord blood stem cells comprise a percentage of CD133+ cells which exceeds said control percentage by a factor of between 2 and 10.

27. The method according to claim 23, wherein the isolated cord blood stem cells further comprise cells other than CD133+ cells, wherein said cells other than CD133+ cells are selected from the group consisting of stem cells from a placenta vascular bed niche, hematopoietic stem cells, mesenchymal stem cells, and combination thereof.

* * * * *